(12) United States Patent
Kajino et al.

(10) Patent No.: US 7,659,267 B2
(45) Date of Patent: Feb. 9, 2010

(54) 1,3-BENZOTHIAZINONE DERIVATIVES, PROCESS FOR PRODUCING THE SAME USE THEREOF

(75) Inventors: Masahiro Kajino, Osaka (JP); Yutaka Nakayama, Sapporo (JP); Haruhide Kimura, Tsukuba (JP)

(73) Assignee: Takeda Pharmaceutical Company Limited, Osaka-Shi (JP)

( * ) Notice: Subject to any disclaimer, the term of this patent is extended or adjusted under 35 U.S.C. 154(b) by 312 days.

(21) Appl. No.: 10/537,520

(22) PCT Filed: Dec. 4, 2003

(86) PCT No.: PCT/JP03/15535

§ 371 (c)(1),
(2), (4) Date: Sep. 1, 2005

(87) PCT Pub. No.: WO2004/060881

PCT Pub. Date: Jul. 22, 2004

(65) Prior Publication Data

US 2006/0052371 A1 Mar. 9, 2006

(30) Foreign Application Priority Data

Dec. 5, 2002 (JP) ............... 2002-353546

(51) Int. Cl.
C07D 279/16 (2006.01)
A61K 31/5415 (2006.01)

(52) U.S. Cl. ..................... 514/226.5; 544/50
(58) Field of Classification Search ............ 544/50; 514/226.5
See application file for complete search history.

(56) References Cited

U.S. PATENT DOCUMENTS

| 3,470,168 | A | 9/1969 | Wolf et al. |
| 2003/0186971 | A1 | 10/2003 | Kimura et al. |

FOREIGN PATENT DOCUMENTS

| JP | 3229241 | 10/1991 |
| WO | WO 02/18356 | 3/2002 |
| WO | WO 02/44157 | 6/2002 |
| WO | WO 03/020719 | 3/2003 |
| WO | WO 03/090782 | 11/2003 |

OTHER PUBLICATIONS

Gade et al. Chemische Berichte (1992), 125(1), 127-141.*
Conti et al. Bollettino Scientifico della Facolta di Chimica Industriale di Bologna (1957), 15, 37-39.*
Conti, L., et al., "Su Alcune Aril-Cheto-Benzo-M-Tiazine", *Bollettino Scientifico Della Facolta Di Chimica Industriale Di Bologna*, (1957), vol. 15, pp. 37-39.
Bourgoin-Legay, D., et al., "Contribution a la Synthese et a l'etude de Benzothiazine-1,3, Etude Chimique Des Composes Obtenus", *Bulletin De La Societe Chimique De France*, (1969), No. 7, pp. 2524-2530.
Simchen, G., et al., "Synthese von Derivaten der 1,3-Benzothiazine-(4) und Des 1,3-Benzoselenazinons-(4)", *Chemische Berichte*, (1970), vol. 103, pp. 413-425.
Gade, T., et al., "Bildung Benzoanellierter Schwefelheterocyclen durch Intramolekulare Kathodische Cyclisierung von Dithiocarbonsaureestern", *Chem. Ber.*, (1992) vol. 125, pp. 127-141.
Perkins, E., et al., "Novel Inhibitors of Poly(ADP-ribose) Polymerase/PARP1 and PARP2 Identified Using a Cell-based Screen in Yeast", *Cancer Research*, (2001), vol. 61, pp. 4175-4183.

\* cited by examiner

*Primary Examiner*—Kahsay T Habte
(74) *Attorney, Agent, or Firm*—Edwards Angell Palmer & Dodge LLP; David G. Conlin; Dwight D. Kim

(57) ABSTRACT

As prophylactic and/or therapeutic agents for cardiovascular diseases, bone or joint diseases, infectious diseases, inflammatory diseases, kidney diseases, etc. having safe and excellent effects of cell death inhibition, MIF binding, etc., there are provided compounds represented by formula:

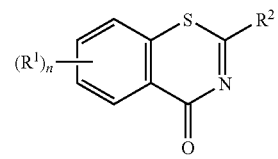

[wherein, $R^1$ represents a halogen atom, etc., $R^2$ represents a group represented by formula:

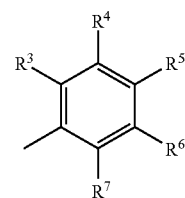

(wherein, $R^3$ represents hydrogen atom, an optionally substituted alkoxy, etc., $R^4$ represents hydrogen atom, bromine atom, cyano, etc., $R^5$ represents hydrogen atom, hydroxy, etc., $R^6$ represents hydrogen atom, etc., $R^7$ represents hydrogen atom, etc.) etc., and n represents an integer of 0 to 4] or salts thereof.

11 Claims, No Drawings

SEQUENCE LISTING

```
<160> NUMBER OF SEQ ID NOS: 2

<210> SEQ ID NO 1
<211> LENGTH: 42
<212> TYPE: DNA
<213> ORGANISM: Rattus norvegicus

<400> SEQUENCE: 1
gagcttggaa atggcattgc taatggtgac aaagcaactt tg            42

<210> SEQ ID NO 2
<211> LENGTH: 42
<212> TYPE: DNA
<213> ORGANISM: Artificial Sequence
<220> FEATURE:
<223> OTHER INFORMATION: mutant ARE
```

```
<400> SEQUENCE: 2
gagcttggaa atggcattgc taatggtggc aaagcaactt tg                    42
```

1,3-BENZOTHIAZINONE DERIVATIVES, PROCESS FOR PRODUCING THE SAME USE THEREOF

TECHNICAL FIELD

The present invention relates to novel 1,3-benzothiazinone derivatives, which is useful as pharmaceuticals, and processes for producing the same, as well as use thereof.

BACKGROUND ART

Apoptosis is closely involved in morphogenesis and histogenesis in the development process of the organism, maintenance of homeostasis, biological defense, etc. and is cell death having an important role in maintaining individual lives. When the death process regulated by genes is congenitally or postnatally hindered, apoptosis is excessively induced or inhibited to cause functional disorders in various organs and thus illness (Saishin Igaku, 54, 825, 1999).

In recent years, it has been revealed that apoptosis is closely involved in onset or progress of various heart diseases (The New England Journal of Medicine, 341, 759, 1999). In a mammalian heart, it is considered that cardiomyocytes are finally differentiated cells and their proliferation activity is lost. Accordingly, when cardiomyocytes are lost due to apoptosis, the heart contraction should be maintained only by the surviving cardiomyocytes. It is thus considered that the loss of cardiomyocytes beyond the threshold necessary for maintaining the heart contraction would result in abnormal heart functions to cause diseases. In fact, apoptosis of cardiomyocytes is observed in various animal models with heart failure or in human patients with heart failure, indicating that disappearance or loss of cardiomyocytes due to apoptosis may contribute to the onset and progress of heart failure (The New England Journal of Medicine, 335, 1182, 1996). It is further recognized that in cardiomyocytes of human patients with heart failure, an apoptosis inhibitory factor Bcl-2 is expressed in excess, which is a possible compensation mechanism for heart failure (The New England Journal of Medicine, 336, 1131, 1997); that serum levels of soluble Fas (sFas, which has an apoptosis inhibitory activity), which lacks a membrane penetration domain in the Fas receptor known as an apoptosis inducing receptor, are increased significantly in proportion to severity in NYHA class (New York Heart Association Functional Class) but independently of fundamental diseases, and thus an increase in serum levels of sFas is considered to be a compensatory mechanism to inhibit promotion of apoptosis in heart failure (Journal of the American College of Cardiology, 29, 1214, 1997). It is also recognized that in the heart with congestive cardiomyopathy, deoxyribonuclease I (DNase I) considered as a indicator of apoptosis is increased 7-fold or more, as compared to healthy persons (Journal of Molecular & Cell Cardiology, 28, 95, 1996).

When considered at the level of internal organs, the functions of the heart muscle are lowered in human cardiac diseases and failure of myocardial contraction often endangers the maintenance of the life. Abnormalities including myocardial disorders, abnormal heart pumping, pressure load due to hypertension, etc., volume load due to acute nephritis, etc, and insufficient blood pumping caused by these abnormalities lead to the onset of heart failure. Against these abnormalities, the sympathetic nervous system, the endocrine system, and the like work together to serve as a compensatory mechanism, which results in cardiac hypertrophy accompanied by hypertrophy of cardiomyocytes. However, when these abnormalities occur alone or in combination persistently and chronically, the hypertrophied cardiomyocytes are not sufficiently supplied with blood, and thus the cardiomyocytes are lost due to apoptosis, etc. As a result, the compensatory mechanism fails to work, leading to a heart failure syndrome accompanied by myocardiopathies such as myocardial stunning, reduced cardiac output, circulatory disorders in internal organs, venostasis, fluid retention, etc.

At present, the heart failure syndrome is treated by using cardiotonic glycosides such as digoxin, etc., sympathetic agents such as dobutamine, etc., phosphodiesterase inhibitors such as amrinone, etc., vasodilators such as hydralazine, calcium antagonists, angiotensin converting enzyme inhibitors, angiotensin receptor antagonists, etc., and congestive cardiomyopathy is treated by β-blockers, etc.

On the other hand, 1,3-benzothiazinone compounds substituted with phenyl at the 2-position are reported in Chemical Abstracts, 119:122687, Chemical Abstracts, 119:16999, Chemical Abstracts, 117:200467, Chemical Abstracts, 116:214422, Chemical Abstracts, 116:21013, Chemical Abstracts, 112:215913, Tetrahedron, 44, 2985-2992, 1988, Chemical Abstracts, 105:144960, Chemical Abstracts, 103:37436, Chemische Berichte, 108, 2523-2530, 1975, Chemical Abstracts, 93:167097, Chemical Abstracts, 85:21262, Chemical Abstracts, 71:91408 and JPA No. 3-229241, but any relation to a macrophage migration inhibitory factor is not described therein.

Furthermore, 1,3-benzothiazinone compounds having a cardiomyocyte apoptosis inhibitory activity are disclosed in WO 02/18356, specifically 2-(2-pyridyl)-4H-1,3-benzothiazin-4-one, 2-(3-pyridyl)-4H-1,3-benzothiazin-4-one, 2-(4-pyridyl)-4H-1,3-benzothiazin-4-one, 2-(4-oxo-3,4-dihydro-2H-1,3-benzothiazin-2-ylidene) ethyl acetate and 2-[2-oxo-2-(1-piperidinyl)ethylidene]-2,3-dihydro-4H-1,3-benzothiazin-4-one.

DISCLOSURE OF THE INVENTION

Drugs for treating heart failure syndrome used so far are not fully satisfactory in their effects. Thus, safe drugs having excellent preventive or therapeutic effects on the heart failure syndrome have been desired.

Considering that inhibition of myocardial apoptosis would be effective for the prevention and treatment of heart failure syndrome, the present inventor has made various studies and as a result, have first synthesized compounds represented by formula:

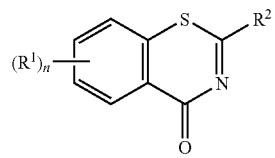

[wherein, $R^1$ represents a halogen atom, hydroxy, nitro, an optionally halogenated alkyl, an acyl or an optionally substituted amino, $R^2$ represents an optionally substituted branched alkyl, an optionally substituted cycloalkyl, an optionally substituted fused homocyclic group, or a group represented by formula:

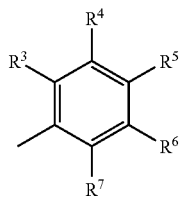

(wherein, $R^3$ and $R^7$ each independently represents (i) hydrogen atom, (ii) fluorine atom, (iii) bromine atom, (iv) nitro, (v) cyano, (vi) an optionally substituted alkyl, (vii) an optionally substituted alkoxy (viii) an optionally substituted aryl, (ix) an acyl, (x) an optionally substituted alkylsulfonyl (xi) an optionally substituted carbamoyl or (xii) an optionally substituted amino; $R^4$ and $R^6$ each independently represents (i) hydrogen atom, (ii) fluorine atom, (iii) bromine atom, (iv) hydroxy (v) cyano, (vi) an alkyl having a substituent selected from carboxy, a halogen atom, an alkoxycarbonyl and an arylcarbonylamino (vii) an optionally substituted alkoxy (viii) an optionally substituted aryl, (ix) an acyl, (x) an optionally substituted alkylsulfonyl (xi) an optionally substituted carbamoyl (xii) an optionally substituted amino or (xiii) an optionally substituted alkoxycarbonyl; and $R^5$ represents (i) hydrogen atom, (ii) fluorine atom, (iii) hydroxy (iv) cyano, (v) an alkyl substituted with a halogen atom, (vi) an optionally substituted aryl, (vii) an acyl, (viii) an optionally substituted carbamoyl or (ix) an optionally substituted amino (provided that the compounds wherein all of $R^3$ to $R^7$ represent hydrogen atoms are excluded)); and n represents 0 to 4] or salts thereof [hereinafter sometimes simply referred to as compound (I)], which are characteristic of chemical structure in having at the 2-position of the 1,3-benzothiazinone skeleton (1) an optionally substituted branched alkyl, (2) an optionally substituted cycloalkyl, (3) an optionally substituted fused homocyclic group or (4) a phenyl having a specific substituent. The inventor has found that unexpectedly this compound (I) possesses an excellent cell death inhibitory effect and is capable of binding to a macrophage migration inhibitory factor, based on its peculiar chemical structure, and further has excellent properties as drugs for the prevention and treatment for heart failure syndrome, etc. Based on these findings, the present invention has been accomplished.

That is, the present invention provides the following features, and so on.

[1] A compound represented by formula:

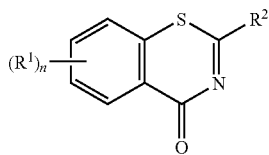

[wherein, $R^1$ represents (1) a halogen atom, (2) hydroxy (3) nitro, (4) an optionally halogenated alkyl, (5) an acyl or (6) an optionally substituted amino; $R^2$ represents (1) an optionally substituted branched alkyl, (2) an optionally substituted cycloalkyl, (3) an optionally substituted fused homocyclic group, or (4) a group represented by formula:

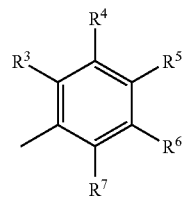

(wherein, $R^3$ and $R^7$ each independently represents (i) hydrogen atom, (ii) fluorine atom, (iii) bromine atom, (iv) nitro, (v) cyano, (vi) an optionally substituted alkyl, (vii) an optionally substituted alkoxy (viii) an optionally substituted aryl, (ix) an acyl, (x) an optionally substituted alkylsulfonyl (xi) an optionally substituted carbamoyl or (xii) an optionally substituted amino; $R^4$ and $R^6$ each independently represents (i) hydrogen atom, (ii) fluorine atom, (iii) bromine atom, (iv) hydroxy (v) cyano, (vi) an alkyl having a substituent selected from carboxy, a halogen atom, an alkoxycarbonyl and an arylcarbonylamino (vii) an optionally substituted alkoxy (viii) an optionally substituted aryl, (ix) an acyl, (x) an optionally substituted alkylsulfonyl (xi) an optionally substituted carbamoyl (xii) an optionally substituted amino or (xiii) an optionally substituted alkoxycarbonyl; and $R^5$ represents (i) hydrogen atom, (ii) fluorine atom, (iii) hydroxy (iv) cyano, (v) an alkyl substituted with a halogen atom, (vi) an optionally substituted aryl, (vii) an acyl, (viii) an optionally substituted carbamoyl or (ix) an optionally substituted amino (provided that the compounds wherein all of $R^3$ to $R^7$ represent hydrogen atoms are excluded)); and n represents an integer of 0 to 4], or a salt thereof;

[2] The compound according to [1], wherein $R^4$ and $R^6$ each independently represents (i) hydrogen atom, (ii) fluorine atom, (iii) bromine atom, (iv) hydroxy (v) cyano, (vi) a carboxy-substituted alkyl, (vii) an optionally substituted alkoxy (viii) an optionally substituted aryl, (ix) an acyl, (x) an optionally substituted alkylsulfonyl (xi) an optionally substituted carbamoyl, or (xii) an optionally substituted amino;

[3] The compound according to [1], wherein,
$R^1$ represents:
(1) a halogen atom;
(2) hydroxy;
(3) nitro;
(4) an optionally halogenated $C_{1-6}$ alkyl;
(5) a $C_{1-6}$ alkyl-carbonyl optionally having 1 to 5 substituents selected from (1') a halogen atom, (2') a $C_{1-3}$ alkylenedioxy (3') nitro, (4') cyano, (5') a $C_{1-6}$ alkyl which may be substituted with 1 to 5 halogen atoms, (6') a $C_{2-6}$ alkenyl which may be substituted with 1 to 5 halogen atoms, (7') a carboxy-$C_{2-6}$ alkenyl, (8') a $C_{2-6}$ alkynyl which may be substituted with 1 to 5 halogen atoms, (9') a $C_{3-8}$ cycloalkyl which may be substituted with 1 to 5 halogen atoms, (10') a $C_{6-14}$ aryl, (11') a $C_{1-6}$ alkoxy which may be substituted with 1 to 5 halogen atoms, (12') a $C_{1-6}$ alkoxy-carbonyl-$C_{1-6}$ alkoxy (13') hydroxy (14') a $C_{6-14}$ aryloxy (15') a $C_{7-16}$ aralkyloxy (16') mercapto, (17') a $C_{1-6}$ alkylthio which may be substituted with 1 to 5 halogen atoms, (18') a $C_{6-14}$ arylthio, (19') a $C_{7-16}$ aralkylthio, (20') amino (21') a mono-$C_{1-6}$ alkylamino (22') a mono-$C_{6-14}$ arylamino (23') a di-$C_{1-6}$ alkylamino (24') a di-$C_{6-14}$ arylamino (25') formyl, (26') carboxy (27') a $C_{1-6}$ alkyl-carbonyl, (28') a $C_{3-8}$ cycloalkyl-carbonyl, (29') a $C_{1-6}$ alkoxy-carbonyl, (30') a $C_{6-14}$ aryl-carbonyl, (31') a $C_{7-16}$ aralkyl-carbonyl, (32') a $C_{6-14}$ aryloxy-carbonyl, (33') a $C_{7-16}$ aralkyloxy-carbonyl, (34') a 5- or 6-membered heterocyclic carbonyl, (35') carbamoyl (36') a mono-$C_{1-6}$alkyl-carbamoyl (37') a di-$C_{1-6}$ alkyl-carbamoyl (38') a mono-$C_{6-14}$ aryl-carbamoyl (39') a 5- or 6-membered heterocyclic carbamoyl (40') a $C_{1-6}$ alkylsulfonyl (41') a $C_{6-14}$ arylsulfonyl (42') formylamino (43') a $C_{1-6}$ alkyl-carbonylamino (44') a $C_{6-14}$ aryl-carbonylamino (45') a $C_{1-6}$ alkoxy-carbonylamino (46') a $C_{1-6}$ alkylsulfonylamino (47') a $C_{6-14}$ arylsulfonylamino (48') a $C_{1-6}$ alkyl-carbonyloxy (49') a $C_{6-14}$ aryl-carbonyloxy (50') a $C_{1-6}$ alkoxy-carbonyloxy (51') a mono-$C_{1-6}$alkyl-carbamoyloxy (52') a di-$C_{1-6}$alkyl-carbamoyloxy (53') a mono-$C_{6-14}$ aryl-carbamoyloxy (54') nicotinoyloxy (55') a 5- to 7-membered saturated cyclic amino (56') a 5- to 10-membered aromatic heterocyclic group and (57') sulfo (hereinafter simply referred to as Substituent group A);

(6) a $C_{2-6}$ alkenyl-carbonyl optionally having 1 to 5 substituents selected from the Substituent group A;

(7) a $C_{2-6}$ alkynyl-carbonyl optionally having 1 to 5 substituents selected from the Substituent group A;

(8) a $C_{3-8}$ cycloalkyl-carbonyl optionally having 1 to 5 substituents selected from the Substituent group A;

(9) a $C_{6-14}$ arylcarbonyl optionally having 1 to 5 substituents selected from the Substituent group A;

(10) a $C_{7-16}$ aralkyl-carbonyl optionally having 1 to 5 substituents selected from the Substituent group A;

(11) a 5- to 14-membered heterocyclic carbonyl containing 1 to 4 hetero atoms, which are 1 or 2 different atoms selected from nitrogen, sulfur and oxygen atoms, in addition to carbon atoms (this heterocyclic carbonyl may have 1 to 5 substituents selected from the Substituent group A);

(12) an amino optionally having 1 or 2 substituents selected from (1') a $C_{1-6}$ alkyl optionally having 1 to 5 substituents selected from the Substituent group A (2') a $C_{2-6}$ alkenyl optionally having 1 to 5 substituents selected from the Substituent group A (3') a $C_{2-6}$ alkynyl optionally having 1 to 5 substituents selected from the Substituent group A (4') a $C_{3-8}$ cycloalkyl optionally having 1 to 5 substituents selected from the Substituent group A (5') a $C_{6-14}$ aryl optionally having 1 to 5 substituents selected from the Substituent group A (6') a $C_{7-16}$ aralkyl optionally having 1 to 5 substituents selected from the Substituent group A (7') a 5- to 14-membered heterocyclic group containing 1 to 4 hetero atoms, which are 1 or 2 different atoms selected from nitrogen, sulfur and oxygen atoms, in addition to carbon atoms, (8') a $C_{1-6}$ alkyl-carbonyl optionally having 1 to 5 substituents selected from the Substituent group A (9') a $C_{2-6}$ alkenyl-carbonyl optionally having 1 to 5 substituents selected from the Substituent group A (10') a $C_{2-6}$ alkynyl-carbonyl optionally having 1 to 5 substituents selected from the Substituent group A (11') a $C_{3-8}$ cycloalkyl-carbonyl optionally having 1 to 5 substituents selected from the Substituent group A (12') a $C_{6-14}$ arylcarbonyl optionally having 1 to 5 substituents selected from the Substituent group A (13') a $C_{7-16}$ aralkyl-carbonyl optionally having 1 to 5 substituents selected from the Substituent group A and (14') a 5- to 14-membered heterocyclic carbonyl containing 1 to 4 hetero atoms, which are 1 or 2 different atoms selected from nitrogen, sulfur and oxygen atoms, in addition to carbon atoms;

$R^2$ represents:

(1) a branched $C_{3-6}$ alkyl optionally having 1 to 5 substituents selected from the Substituent group A;

(2) a $C_{3-8}$ cycloalkyl optionally having 1 to 5 substituents selected from the Substituent group A;

(3) a $C_{9-14}$ fused homocyclic group optionally having 1 to 5 substituents selected from the Substituent group A; or, (4) a group represented by formula:

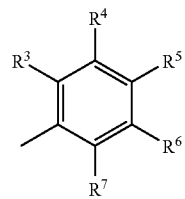

(wherein:

$R^3$ and $R^7$ each independently represents:

(1) hydrogen atom;

(2) fluorine atom;

(3) bromine atom;

(4) nitro;

(5) cyano;

(6) a $C_{1-6}$ alkyl optionally having 1 to 5 substituents selected from the Substituent group A;

(7) a $C_{1-6}$ alkoxy optionally having 1 to 5 substituents selected from the Substituent group A;

(8) a $C_{6-14}$ aryl optionally having 1 to 5 substituents selected from the Substituent group A;

(9) a $C_{1-6}$ alkyl-carbonyl optionally having 1 to 5 substituents selected from the Substituent group A;

(10) a $C_{2-6}$ alkenyl-carbonyl optionally having 1 to 5 substituents selected from the Substituent group A;

(11) a $C_{2-6}$ alkynyl-carbonyl optionally having 1 to 5 substituents selected from the Substituent group A;

(12) a $C_{3-8}$ cycloalkyl-carbonyl optionally having 1 to 5 substituents selected from the Substituent group A;

(13) a $C_{6-14}$ aryl-carbonyl optionally having 1 to 5 substituents selected from the Substituent group A;

(14) a $C_{7-16}$ aralkyl-carbonyl optionally having 1 to 5 substituents selected from the Substituent group A;

(15) a 5- to 14-membered heterocyclic carbonyl containing 1 to 4 hetero atoms, which are 1 or 2 different atoms selected from nitrogen, sulfur and oxygen atoms, in addition to carbon atoms;

(16) a $C_{1-6}$ alkylsulfonyl optionally having 1 to 5 substituents selected from the Substituent group A;

(17) a carbamoyl optionally having 1 or 2 substituents selected from (1') a $C_{1-6}$ alkyl optionally having 1 to 5 substituents selected from the Substituent group A (2') a $C_{2-6}$ alkenyl optionally having 1 to 5 substituents selected from the Substituent group A (3') a $C_{2-6}$ alkynyl optionally having 1 to 5 substituents selected from the Substituent group A (4') a $C_{3-8}$ cycloalkyl optionally having 1 to 5 substituents selected from the Substituent group A (5') a $C_{6-14}$ aryl optionally having 1 to 5 substituents selected from the Substituent group A (6') a $C_{7-16}$ aralkyl optionally having 1 to 5 substituents selected from the Substituent group A (7') a 5- to 14-membered heterocyclic carbonyl containing 1 to 4 hetero atoms, which are 1 or 2 different atoms selected from nitrogen, sulfur and oxygen atoms, in addition to carbon atoms, (8') a $C_{1-6}$ alkyl-carbonyl optionally having 1 to 5 substituents selected from the Substituent group A (9') a $C_{2-6}$ alkenyl-carbonyl optionally having 1 to 5 substituents selected from the Substituent group A (10') a $C_{2-6}$ alkynyl-carbonyl optionally having 1 to 5 substituents selected from the Substituent group A (11') a $C_{3-8}$ cycloalkyl-carbonyl optionally having 1 to 5 substituents selected from the Substituent group A (12') a $C_{6-14}$ aryl-carbonyl optionally having 1 to 5 substituents selected from the Substituent group A (13') a $C_{7-16}$ aralkyl-carbonyl optionally having 1 to 5 substituents selected from the Substituent group A and (14') a 5- to 14-membered heterocyclic carbonyl containing 1 to 4 hetero atoms, which are 1 or 2 different atoms selected from nitrogen, sulfur and oxygen atoms, in addition to carbon atoms; or,

(18) an amino optionally having 1 or 2 substituents selected from (1') a $C_{1-6}$ alkyl optionally having 1 to 5 substituents selected from the Substituent group A (2') a $C_{2-6}$ alkenyl optionally having 1 to 5 substituents selected from the Substituent group A (3') a $C_{2-6}$ alkynyl optionally having 1 to 5 substituents selected from the Substituent group A (4') a $C_{3-8}$ cycloalkyl optionally having 1 to 5 substituents selected from the Substituent group A (5') a $C_{6-14}$ aryl optionally having 1 to 5 substituents selected from the Substituent group A (6') a $C_{7-16}$ aralkyl optionally having 1 to 5 substituents selected from the Substituent group A (7') a 5- to 14-membered heterocyclic carbonyl containing 1 to 4 hetero atoms, which are 1 or 2 different atoms selected from nitrogen, sulfur and oxygen atoms, in addition to carbon atoms, (8') a $C_{1-6}$ alkyl-carbonyl optionally having 1 to 5 substituents selected from the Substituent group A (9') a $C_{2-6}$ alkenyl-carbonyl optionally having 1 to 5 substituents selected from the Substituent group A (10') a $C_{2-6}$ alkynyl-carbonyl optionally having 1 to 5 substituents selected from the Substituent group A (11') a $C_{3-8}$ cycloalkyl-carbonyl optionally having 1 to 5 substituents selected from the Substituent group A (12') a $C_{6-14}$ aryl-carbonyl optionally having 1 to 5 substituents selected from the Substituent group A (13') a $C_{7-16}$ aralkyl-carbonyl optionally having 1 to 5 substituents selected from the Substituent group A and (14') a 5- to 14-membered heterocyclic carbonyl containing 1 to 4 hetero atoms, which are 1 or 2 different atoms selected from nitrogen, sulfur and oxygen atoms, in addition to carbon atoms; and, $R^4$ and $R^6$ each independently represents:

(1) hydrogen atom;
(2) fluorine atom;
(3) bromine atom;
(4) hydroxy;
(5) cyano;
(6) a $C_{1-6}$ alkyl having 1 to 3 substituents selected from carboxy, a halogen atom, a $C_{1-6}$ alkoxy-carbonyl and a $C_{6-14}$ aryl-carbonylamino;
(7) a $C_{1-6}$ alkoxy optionally having 1 to 5 substituents selected from the Substituent group A;
(8) a $C_{6-14}$ aryl optionally having 1 to 5 substituents selected from the Substituent group A;
(9) a $C_{1-6}$ alkyl-carbonyl optionally having 1 to 5 substituents selected from the Substituent group A;
(10) a $C_{2-6}$ alkenyl-carbonyl optionally having 1 to 5 substituents selected from the Substituent group A;
(11) a $C_{2-6}$ alkynyl-carbonyl optionally having 1 to 5 substituents selected from the Substituent group A;
(12) a $C_{3-8}$ cycloalkyl-carbonyl optionally having 1 to 5 substituents selected from the Substituent group A;
(13) a $C_{6-14}$ aryl-carbonyl optionally having 1 to 5 substituents selected from the Substituent group A;
(14) a $C_{7-16}$ aralkyl-carbonyl optionally having 1 to 5 substituents selected from the Substituent group A;
(15) a 5- to 14-membered heterocyclic carbonyl containing 1 to 4 hetero atoms, which are 1 or 2 different atoms selected from nitrogen, sulfur and oxygen atoms, in addition to carbon atoms;
(16) a $C_{1-6}$ alkylsulfonyl optionally having 1 to 5 substituents selected from the Substituent group A;
(17) a carbamoyl optionally having substituents selected from (1') a $C_{1-6}$ alkyl optionally having 1 to 5 substituents selected from the Substituent group A (2') a $C_{2-6}$ alkenyl optionally having 1 to 5 substituents selected from the Substituent group A (3') a $C_{2-6}$ alkynyl optionally having 1 to 5 substituents selected from the Substituent group A (4') a $C_{3-8}$ cycloalkyl optionally having 1 to 5 substituents selected from the Substituent group A (5') a $C_{6-14}$ aryl optionally having 1 to 5 substituents selected from the Substituent group A (6') a $C_{7-16}$ aralkyl optionally having 1 to 5 substituents selected from the Substituent group A (7') a 5- to 14-membered heterocyclic carbonyl containing 1 to 4 hetero atoms, which are 1 or 2 different atoms selected from nitrogen, sulfur and oxygen atoms, in addition to carbon atoms, (8') a $C_{1-6}$ alkyl-carbonyl optionally having 1 to 5 substituents selected from the Substituent group A (9') a $C_{2-6}$ alkenyl-carbonyl optionally having 1 to 5 substituents selected from the Substituent group A (10') a $C_{2-6}$ alkynyl-carbonyl optionally having 1 to 5 substituents selected from the Substituent group A (11') a $C_{3-8}$ cycloalkyl-carbonyl optionally having 1 to 5 substituents selected from the Substituent group A (12') a $C_{6-14}$ aryl-carbonyl optionally having 1 to 5 substituents selected from the Substituent group A (13') a $C_{7-16}$ aralkyl-carbonyl optionally having 1 to 5 substituents selected from the Substituent group A and (14') a 5- to 14-membered heterocyclic carbonyl containing 1 to 4 hetero atoms, which are 1 or 2 different atoms selected from nitrogen, sulfur and oxygen atoms, in addition to carbon atoms;

(18) an amino optionally having 1 or 2 substituents selected from (1') a $C_{1-6}$ alkyl optionally having 1 to 5 substituents selected from the Substituent group A (2') a $C_{2-6}$ alkenyl optionally having 1 to 5 substituents selected from the Substituent group A (3') a $C_{2-6}$ alkynyl optionally having 1 to 5 substituents selected from the Substituent group A (4') a $C_{3-8}$ cycloalkyl optionally having 1 to 5 substituents selected from the Substituent group A (5') a $C_{6-14}$ aryl optionally having 1 to 5 substituents selected from the Substituent group A (6') a $C_{7-16}$ aralkyl optionally having 1 to 5 substituents selected from the Substituent group A (7') a 5- to 14-membered heterocyclic carbonyl containing 1 to 4 hetero atoms, which are 1 or 2 different atoms selected from nitrogen, sulfur and oxygen atoms, in addition to carbon atoms, (8') a $C_{1-6}$ alkyl-carbonyl optionally having 1 to 5 substituents selected from the Substituent group A (9') a $C_{2-6}$ alkenyl-carbonyl optionally having 1 to 5 substituents selected from the Substituent group A (10') a $C_{2-6}$ alkynyl-carbonyl optionally having 1 to 5 substituents selected from the Substituent group A (11') a $C_{3-8}$ cycloalkyl-carbonyl optionally having 1 to 5 substituents selected from the Substituent group A (12') a $C_{6-14}$ aryl-carbonyl optionally having 1 to 5 substituents selected from the Substituent group A (13') a $C_{7-16}$ aralkyl-carbonyl optionally having 1 to 5 substituents selected from the Substituent group A and (14') a 5- to 14-membered heterocyclic carbonyl containing 1 to 4 hetero atoms, which are 1 or 2 different atoms selected from nitrogen, sulfur and oxygen atoms, in addition to carbon atoms or

(19) a $C_{1-6}$ alkoxy-carbonyl optionally having 1 to 5 substituents selected from the Substituent group A;

$R^5$ represents:

(1) hydrogen atom;
(2) fluorine atom;
(3) hydroxy;
(4) cyano;
(5) a $C_{1-6}$ alkyl substituted with 1 to 5 halogen atoms;
(6) a $C_{6-14}$ aryl optionally having 1 to 5 substituents selected from the Substituent group A;

(7) a $C_{1-6}$ alkyl-carbonyl optionally having 1 to 5 substituents selected from the Substituent group A;
(8) a $C_{2-6}$ alkenyl-carbonyl optionally having 1 to 5 substituents selected from the Substituent group A;
(9) a $C_{2-6}$ alkynyl-carbonyl optionally having 1 to 5 substituents selected from the Substituent group A;
(10) a $C_{3-8}$ cycloalkyl-carbonyl optionally having 1 to 5 substituents selected from the Substituent group A;
(11) a $C_{6-14}$ aryl-carbonyl optionally having 1 to 5 substituents selected from the Substituent group A;
(12) a $C_{7-16}$ aralkyl-carbonyl optionally having 1 to 5 substituents selected from the Substituent group A;
(13) a 5- to 14-membered heterocyclic carbonyl containing 1 to 4 hetero atoms, which are 1 or 2 different atoms selected from nitrogen, sulfur and oxygen atoms, in addition to carbon atoms;
(14) a carbamoyl optionally having 1 or 2 substituents selected from (1') a $C_{1-6}$ alkyl optionally having 1 to 5 substituents selected from the Substituent group A (2') a $C_{2-6}$ alkenyl optionally having 1 to 5 substituents selected from the Substituent group A (3') a $C_{2-6}$ alkynyl optionally having 1 to 5 substituents selected from the Substituent group A (4') a $C_{3-8}$ cycloalkyl optionally having 1 to 5 substituents selected from the Substituent group A (5') a $C_{6-14}$ aryl optionally having 1 to 5 substituents selected from the Substituent group A (6') a $C_{7-16}$ aralkyl optionally having 1 to 5 substituents selected from the Substituent group A (7') a 5- to 14-membered heterocyclic carbonyl containing 1 to 4 hetero atoms, which are 1 or 2 different atoms selected from nitrogen, sulfur and oxygen atoms, in addition to carbon atoms, (8') a $C_{1-6}$ alkyl-carbonyl optionally having 1 to 5 substituents selected from the Substituent group A (9') a $C_{2-6}$ alkenyl-carbonyl optionally having 1 to 5 substituents selected from the Substituent group A (10') a $C_{2-6}$ alkynyl-carbonyl optionally having 1 to 5 substituents selected from the Substituent group A (11') a $C_{3-8}$ cycloalkyl-carbonyl optionally having 1 to 5 substituents selected from the Substituent group A (12') a $C_{6-14}$ aryl-carbonyl optionally having 1 to 5 substituents selected from the Substituent group A (13') a $C_{7-16}$ aralkyl-carbonyl optionally having 1 to 5 substituents selected from the Substituent group A and (14') a 5- to 14-membered heterocyclic carbonyl containing 1 to 4 hetero atoms, which are 1 or 2 different atoms selected from nitrogen, sulfur and oxygen atoms, in addition to carbon atoms, or
(15) an amino optionally having 1 or 2 substituents selected from (1') a $C_{1-6}$ alkyl optionally having 1 to 5 substituents selected from the Substituent group A (2') a $C_{2-6}$ alkenyl optionally having 1 to 5 substituents selected from the Substituent group A (3') a $C_{2-6}$ alkynyl optionally having 1 to 5 substituents selected from the Substituent group A (4') a $C_{3-8}$ cycloalkyl optionally having 1 to 5 substituents selected from the Substituent group A (5') a $C_{6-14}$ aryl optionally having 1 to 5 substituents selected from the Substituent group A (6') a $C_{7-16}$ aralkyl optionally having 1 to 5 substituents selected from the Substituent group A (7') a 5- to 14-membered heterocyclic carbonyl containing 1 to 4 hetero atoms, which are 1 or 2 different atoms selected from nitrogen, sulfur and oxygen atoms, in addition to carbon atoms, (8') a $C_{1-6}$ alkyl-carbonyl optionally having 1 to 5 substituents selected from the Substituent group A (9') a $C_{2-6}$ alkenyl-carbonyl optionally having 1 to 5 substituents selected from the Substituent group A (10') a $C_{2-6}$ alkynyl-carbonyl optionally having 1 to 5 substituents selected from the Substituent group A (11') a $C_{3-8}$ cycloalkyl-carbonyl optionally having 1 to 5 substituents selected from the Substituent group A (12') a $C_{6-14}$ aryl-carbonyl optionally having 1 to 5 substituents selected from the Substituent group A (13') a $C_{7-16}$ aralkyl-carbonyl optionally having 1 to 5 substituents selected from the Substituent group A and (14') a 5- to 14-membered heterocyclic carbonyl containing 1 to 4 hetero atoms, which are 1 or 2 different atoms selected from nitrogen, sulfur and oxygen atoms, in addition to carbon atoms); and, n is an integer of 0 to 4;

[4] The compound according to [1], wherein $R^2$ is a branched $C_{3-6}$ alkyl, a $C_{3-8}$ cycloalkyl, or a group represented by formula:

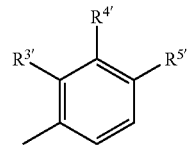

(wherein $R^{3'}$ represents (1) hydrogen atom, (2) a $C_{1-6}$ alkoxy or (3) a $C_{1-6}$ alkyl substituted with 1 to 5 halogen atoms; $R^{4'}$ represents (1) hydrogen atom, (2) bromine atom, (3) cyano, (4) a $C_{1-6}$ alkyl having 1 to 3 substituents selected from carboxy, a halogen atom, a $C_{1-6}$ alkoxy-carbonyl and a $C_{6-14}$ aryl-carbonylamino (5) a $C_{1-6}$ alkoxy substituted with a $C_{1-6}$ alkoxy-carbonyl or (6) a $C_{1-6}$ alkyl-carbonylamino; and $R^{5'}$ represents hydrogen atom, hydroxy, cyano, a $C_{1-6}$ alkyl substituted with 1 to 5 halogen atoms, a $C_{6-14}$ aryl, a $C_{1-6}$ alkyl-carbonyl, a di-$C_{1-6}$alkyl-carbamoyl or a $C_{1-6}$ alkyl-carbonylamino), and n is 0;

[5] The compound according to [1], wherein R is a $C_{3-8}$ cycloalkyl;

[6] The compound according to [1], wherein $R^2$ is a group represented by formula:

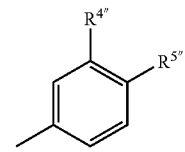

(wherein $R^{4''}$ represents hydrogen atom or cyano, and $R^{5''}$ represents hydrogen atom, a $C_{1-6}$ alkyl-carbonyl or a $C_{1-6}$ alkyl-carbonylamino);

[7] The compound according to [1], which is
2-(3-cyanophenyl)-4H-1,3-benzothiazin-4-one,
2-(4-acetylphenyl)-4H-1,3-benzothiazin-4-one,
2-(4-methylsulfonylphenyl)-4H-1,3-benzothiazin-4-one,
2-(4-acetylaminophenyl)-4H-1,3-benzothiazin-4-one, or
2-(3-trifluoromethylphenyl)-4H-1,3-benzothiazin-4-one;

[8] The compound according to [1], which is capable of binding to a macrophage migration inhibitory factor;

[9] A binder for macrophage migration inhibitory factor consisting of the compound according to [1];

[10] A prodrug of the compound according to [1];

[11] A pharmaceutical composition comprising the compound according to [1] or its prodrug;

[12] The pharmaceutical composition according to [11], which is a cell death inhibitor or a cytoprotective agent;

[13] The pharmaceutical composition according to [11], which is an apoptosis inhibitor;

[14] The pharmaceutical composition according to [11], which is a myocardial cell death inhibitor;

[15] The pharmaceutical composition according to [11], which is an agent for preventing or treating a disease induced by cell death;

[16] The pharmaceutical composition according to [11], which is an agent for preventing or treating a disease caused by a macrophage migration inhibitory factor;

[17] The pharmaceutical composition according to [11], which is an agent for preventing or treating cardiovascular diseases, bone or joint diseases, infectious diseases, inflammatory diseases or kidney diseases;

[18] A method for preventing or treating cardiovascular diseases, bone or joint diseases, infectious diseases, inflammatory diseases or kidney diseases, which comprises administering to a mammal an effective dose of the compound according to [11] or its prodrug;

[19] Use of the compound according to [11] or its prodrug to manufacture an agent for preventing or treating cardiovascular diseases, bone or joint diseases, infectious diseases, inflammatory diseases or kidney diseases.

In Compound (I), $R^1$ represents a halogen atom, hydroxy, nitro, an optionally halogenated alkyl, an acyl or an optionally substituted amino.

The "halogen atom" represented by $R^1$ includes, for example, fluorine, chlorine, bromine, iodine, etc.

The "optionally halogenated alkyl" represented by $R^1$ includes, for example, an alkyl (e.g., methyl, ethyl, propyl, isopropyl, butyl, isobutyl, sec-butyl, tert-butyl, pentyl, hexyl, etc. $C_{1-6}$ alkyl, etc.) optionally having 1 to 5, preferably 1 to 3 halogen atoms (e.g., fluorine, chlorine, bromine, iodine, etc.), etc. Specific examples are methyl, chloromethyl, difluoromethyl, trichloromethyl, trifluoromethyl, ethyl, 2-bromoethyl, 2,2,2-trifluoroethyl, pentafluoroethyl, propyl, 3,3,3-trifluoropropyl, isopropyl, butyl, 4,4,4-trifluorobutyl, isobutyl, sec-butyl, tert-butyl, pentyl, isopentyl, neopentyl, 5,5,5-trifluoropentyl, hexyl, 6,6,6-trifluorohexyl, etc.

The "acyl" represented by $R^1$ includes, for example, formyl, an optionally substituted alkylcarbonyl, an optionally substituted alkenylcarbonyl, an optionally substituted alkynylcarbonyl, an optionally substituted cycloalkylcarbonyl, an optionally substituted arylcarbonyl, an optionally substituted aralkylcarbonyl, an optionally substituted heterocyclic carbonyl, etc.

Examples of the alkylcarbonyl in the "optionally substituted alkylcarbonyl" as the "acyl" represented by $R^1$ include a $C_{1-6}$ alkyl-carbonyl such as methylcarbonyl, ethylcarbonyl, propylcarbonyl, isopropylcarbonyl, butylcarbonyl, isobutylcarbonyl, sec-butylcarbonyl, tert-butylcarbonyl, pentylcarbonyl, hexylcarbonyl, etc.

The substituent in the "optionally substituted alkylcarbonyl" includes (1) a halogen atom (e.g., fluorine, chlorine, bromine, iodine, etc.), (2) a $C_{1-3}$ alkylenedioxy (e.g., methylenedioxy, ethylenedioxy, etc.), (3) nitro, (4) cyano, (5) an optionally halogenated $C_{1-6}$ alkyl (e.g., methyl, ethyl, propyl, isopropyl, butyl, isobutyl, sec-butyl, tert-butyl, pentyl, hexyl, etc., optionally having 1 to 5 (preferably 1 to 3) halogens including fluorine, chlorine, bromine and iodine), (6) an optionally halogenated $C_{2-6}$ alkenyl (e.g., vinyl, propenyl, isopropenyl, 2-buten-1-yl, 4-penten-1-yl, 5-hexen-1-yl, etc., optionally having 1 to 5 (preferably 1 to 3) halogens including fluorine, chlorine, bromine and iodine), (7) a carboxy-$C_{2-6}$ alkenyl (e.g., 2-carboxyethenyl, 2-carboxy-2-methylethenyl, etc.), (8) an optionally halogenated $C_{2-6}$alkynyl(e.g., 2-butyn-1-yl, 4-pentyn-1-yl, 5-hexyn-1-yl, etc., optionally having 1 to 5 (preferably 1 to 3) halogens including fluorine, chlorine, bromine and iodine), (9) an optionally halogenated $C_{3-8}$ cycloalkyl (e.g., cyclopropyl, cyclobutyl, cyclopentyl, cyclohexyl, cycloheptyl, cyclooctyl, etc., optionally having 1 to 5 (preferably 1 to 3) halogens including fluorine, chlorine, bromine and iodine), (10) a $C_{6-14}$ aryl (e.g., phenyl, 1-naphthyl, 2-naphthyl, 2-biphenylyl, 3-biphenylyl, 4-biphenylyl, 2-anthryl, etc.), (11) an optionally halogenated $C_{1-8}$ alkoxy (e.g., methoxy, ethoxy, propoxy, isopropoxy, butoxy, isobutoxy, sec-butoxy, tert-butoxy, pentoxy, hexyloxy, etc., optionally having 1 to 5 (preferably 1 to 3) halogens including fluorine, chlorine, bromine and iodine), (12) a $C_{1-6}$ alkoxycarbonyl-$C_{1-6}$ alkoxy (e.g., ethoxycarbonylmethyloxy, etc.), (13) hydroxy (14) a $C_{6-14}$ aryloxy (e.g., phenyloxy, 1-naphthyloxy, 2-naphthyloxy, etc.), (15) a $C_{7-16}$ aralkyloxy (e.g., benzyloxy, phenethyloxy, etc.), (16) mercapto, (17) an optionally halogenated $C_{1-6}$ alkylthio (e.g., methylthio, ethylthio, propylthio, isopropylthio, butylthio, isobutylthio, sec-butylthio, tert-butylthio, pentylthio, hexylthio, etc., optionally having 1 to 5 (preferably 1 to 3) halogens including fluorine, chlorine, bromine and iodine), (18) a $C_{6-14}$ arylthio (e.g., phenylthio, 1-naphthylthio, 2-naphthylthio, etc.), (19) a $C_{7-16}$ aralkylthio (e.g., benzylthio, phenethylthio, etc.), (20) amino (21) a mono-$C_{1-6}$ alkylamino (e.g., methylamino, ethylamino, etc.), (22) a mono-$C_{6-14}$ arylamino (e.g., phenylamino, 1-naphthylamino, 2-naphthylamino, etc.), (23) a di-$C_{1-6}$ alkylamino (e.g., dimethylamino, diethylamino, ethylmethylamino, etc.), (24) a di-$C_{6-14}$ arylamino (e.g., diphenylamino, etc.), (25) formyl, (26) carboxy (27) a $C_{1-6}$ alkyl-carbonylalkyl-carbonyl (e.g., acetyl, propionyl, etc.), (28) a $C_{3-8}$ cycloalkyl-carbonyl (e.g., cyclopropylcarbonyl, cyclopentylcarbonyl, cyclohexylcarbonyl, cycloheptylcarbonyl, cyclooctylcarbonyl, etc.), (29) a $C_{1-6}$ alkoxy-carbonyl (e.g., methoxycarbonyl, ethoxycarbonyl, propoxycarbonyl, tert-butoxycarbonyl, etc.), (30) a $C_{6-14}$ aryl-carbonyl (e.g., benzoyl, 1-naphthoyl, 2-naphthoyl, etc.), (31) a $C_{7-16}$ aralkyl-carbonyl (e.g., phenylacetyl, 3-phenylpropionyl, etc.), (32) a $C_{6-14}$aryloxy-carbonyl (e.g., phenoxycarbonyl, etc.), (33) a $C_{7-16}$aralkyloxy-carbonyl (e.g., benzyloxycarbonyl, phenethyloxycarbonyl, etc.), (34) a 5- or 6-membered heterocyclic carbonyl (e.g., nicotinoyl, isonicotinoyl, thenoyl, furoyl, morpholinocarbonyl, thiomorpholinocarbonyl, piperazin-1-ylcarbonyl, pyrrolidin-1-ylcarbonyl, etc.), (35) carbamoyl (36) a mono-$C_{1-6}$alkyl-carbamoyl (e.g., methylcarbamoyl, ethylcarbamoyl, etc.), (37) a di-$C_{1-6}$alkyl-carbamoyl (e.g., dimethylcarbamoyl, diethylcarbamoyl, ethylmethylcarbamoyl, etc.), (38) a mono-$C_{6-14}$aryl-carbamoyl (e.g., phenylcarbamoyl, 1-naphthylcarbamoyl, 2-naphthylcarbamoyl, etc.), (39) a 5- or 6-membered heterocyclic carbamoyl (e.g., 2-pyridylcarbamoyl, 3-pyridylcarbamoyl, 4-pyridylcarbamoyl, 2-thienylcarbamoyl, 3-thienylcarbamoyl, etc.), (40) a $C_{1-6}$ alkylsulfonyl (e.g., methylsulfonyl, ethylsulfonyl, etc.), (41) $C_{6-14}$ arylsulfonyl (e.g., phenylsulfonyl, 1-naphthylsulfonyl, 2-naphthylsulfonyl, etc.), (42) formylamino (43) a $C_{1-6}$ alkyl-carbonylalkyl-carbonylamino (e.g., acetylamino, etc.), (44) a $C_{6-14}$aryl-carbonylamino (e.g., benzoylamino, naphthoylamino, etc.), (45) a $C_{1-6}$ alkoxy-carbonylamino (e.g., methoxycarbonylamino, ethoxycarbonylamino, propoxycarbonylamino, butoxycarbonylamino, etc.), (46) a $C_{1-6}$ alkylsulfonylamino (e.g., methylsulfonylamino, ethylsulfonylamino, etc.), (47) a $C_{6-14}$ arylsulfonylamino (e.g., phenylsulfonylamino, 2-naphthylsulfonylamino, 1-naphthylsulfonylamino, etc.), (48) a $C_{1-6}$ alkyl-carbonyloxy (e.g., acetoxy, propionyloxy, etc.), (49) a $C_{6-14}$aryl-carbonyloxy (e.g., benzoyloxy, naphthylcarbonyloxy, etc.), (50) a $C_{1-6}$ alkoxy-carbonyloxy (e.g., methoxycarbonyloxy, ethoxycarbonyloxy, propoxycarbonyloxy, butoxycarbonyloxy, etc.), (51) a mono-$C_{1-6}$alkyl-carbamoyloxy (e.g., methylcarbamoyloxy, ethylcarbamoyloxy, etc.), (52) a di-$C_{1-6}$alkyl-carbamoyloxy (e.g., dimethylcarbamoyloxy, diethylcarbamoyloxy, etc.), (53) a mono-$C_{6-14}$ aryl-carbamoyloxy (e.g., phenylcarbamoyloxy, naphthylcarbamoyloxy, etc.), (54) nicotinoyloxy, (55) a 5- to 7-membered saturated cyclic amino, (56) a 5- to 10-membered aromatic heterocyclic group (e.g., 2-thienyl, 3-thienyl, 2-pyridyl, 3-pyridyl, 4-pyridyl, 2-quinolyl, 3-quinolyl, 4-quinolyl, 5-quinolyl, 8-quinolyl, 1-isoquinolyl, 3-isoquinolyl, 4-isoquinolyl, 5-isoquinolyl, 1-indolyl, 2-indolyl, 3-indolyl, 2-benzothiazolyl, 2-benzo[b]thienyl, 3-benzo[b]thienyl, 2-benzo[b]furanyl, 3-benzo[b]furanyl, etc.), (57) sulfo, etc. The number of substituents may be 1 to 5, preferably 1 to 3, at substitutable positions. When the number of these substituents is 2 or more, the respective substituents may be the same or different.

The alkenylcarbonyl in the "optionally substituted alkenylcarbonyl," which is the "acyl" represented by $R^1$, includes a $C_{2-6}$ alkenyl-carbonyl such as vinylcarbonyl, allylcarbonyl, isopropenylcarbonyl, 1-butenylcarbonyl, 2-butenylcarbonyl, 3-butenylcarbonyl, 2-methyl-2-propenylcarbonyl, 1-methyl-2-propenylcarbonyl, 2-methyl-1-propenylcarbonyl, etc.

In the "optionally substituted alkenylcarbonyl," examples of the substituent are the same as the substituent in the "optionally substituted alkylcarbonyl" described above, with the same number of substituents.

The alkynylcarbonyl in the "optionally substituted alkynylcarbonyl," which is the "acyl" represented by $R^1$, includes a $C_{2-6}$ alkynyl-carbonyl such as ethynylcarbonyl, propargylcarbonyl, 1-butynylcarbonyl, 2-butynylcarbonyl, 3-butynylcarbonyl, 1-hexynylcarbonyl, etc.

In the "optionally substituted alkynylcarbonyl," examples of the substituent are the same as the substituent in the "optionally substituted alkylcarbonyl" described above, with the same number of substituents.

The cycloalkylcarbonyl in the "optionally substituted cycloalkylcarbonyl," which is the "acyl" represented by $R^1$, includes a $C_{3-8}$ cycloalkyl-carbonyl such as cyclopropylcarbonyl, cyclobutylcarbonyl, cyclopentylcarbonyl, cyclohexylcarbonyl, cycloheptylcarbonyl, cyclooctylcarbonyl, etc.

In the "optionally substituted cycloalkylcarbonyl," examples of the substituent are the same as the substituent in the "optionally substituted alkylcarbonyl" described above, with the same number of substituents.

The arylcarbonyl in the "optionally substituted arylcarbonyl," which is the "acyl" represented by $R^1$, includes a $C_{6-14}$ aryl-carbonyl such as benzoyl, 1-naphthoyl, 2-naphthoyl, etc.

In the "optionally substituted arylcarbonyl," examples of the substituent are the same as the substituent in the "optionally substituted alkylcarbonyl" described above, with the same number of substituents.

The aralkylcarbonyl in the "optionally substituted aralkylcarbonyl," which is the "acyl" represented by $R^1$, includes a $C_{7-16}$ aralkyl-carbonyl such as phenylacetyl, 3-phenylpropionyl, etc.

In the "optionally substituted aralkylcarbonyl," examples of the substituent are the same as the substituent in the "optionally substituted alkylcarbonyl" described above, with the same number of substituents.

The heterocyclic carbonyl in the "optionally substituted heterocyclic carbonyl," which is the "acyl" represented by $R^1$, includes a 5- to 14-membered heterocyclic carbonyl containing 1 to 4 hetero atoms, which are 1 or 2 different atoms selected from nitrogen, sulfur and oxygen atoms, in addition to carbon atoms (e.g., an aromatic heterocyclic carbonyl such as 2-thienylcarbonyl, 3-thienylcarbonyl, 2-furylcarbonyl, 3-furylcarbonyl, 2-pyridylcarbonyl, 3-pyridylcarbonyl, 4-pyridylcarbonyl, 2-quinolylcarbonyl, 3-quinolylcarbonyl, 4-quinolylcarbonyl, 5-quinolylcarbonyl, 8-quinolylcarbonyl, 1-isoquinolylcarbonyl, 3-isoquinolylcarbonyl, 4-isoquinolylcarbonyl, 5-isoquinolylcarbonyl, pyrazinylcarbonyl, 2-pyrimidinylcarbonyl, 4-pyrimidinylcarbonyl, 3-pyrrolylcarbonyl, 2-imidazolylcarbonyl, 3-pyridazinylcarbonyl, 3-isothiazolylcarbonyl, 3-isooxazolylcarbonyl, 1-indolylcarbonyl, 2-indolylcarbonyl, 3-indolylcarbonyl, 2-benzothiazolylcarbonyl, 2-benzo[b]thienylcarbonyl, 3-benzo[b]thienylcarbonyl, 2-benzo[b]furanylcarbonyl, 3-benzo[b]furanylcarbonyl, etc.; a non-aromatic heterocyclic carbonyl such as 1-pyrrolidinylcarbonyl, 2-pyrrolidinylcarbonyl, 3-pyrrolidinylcarbonyl, 2-imidazolinylcarbonyl, 4-imidazolinylcarbonyl, 2-pyrazolidinylcarbonyl, 3-pyrazolidinylcarbonyl, 4-pyrazolidinylcarbonyl, piperidinocarbonyl, 2-piperidylcarbonyl, 3-piperidylcarbonyl, 4-piperidylcarbonyl, 1-piperazinylcarbonyl, 2-piperazinylcarbonyl, morpholinocarbonyl, thiomorpholinocarbonyl, etc.).

In the "optionally substituted heterocyclic carbonyl," examples of the substituent are the same as the substituent in the "optionally substituted alkylcarbonyl" described above, with the same number of substituents.

The "optionally substituted amino" represented by $R^1$ includes an amino optionally having 1 or 2 substituents selected from, for example, (1) an optionally substituted alkyl, (2) an optionally substituted alkenyl, (3) an optionally substituted alkynyl, (4) an optionally substituted cycloalkyl, (5) an optionally substituted aryl, (6) an optionally substituted aralkyl, (7) an optionally substituted heterocyclic group (8) an optionally substituted alkylcarbonyl, (9) an optionally substituted alkenylcarbonyl, (10) an optionally substituted alkynylcarbonyl, (11) an optionally substituted cycloalkylcarbonyl, (12) an optionally substituted arylcarbonyl, (13) an optionally substituted aralkylcarbonyl and (14) an optionally substituted heterocyclic carbonyl.

The alkyl in the "optionally substituted alkyl" as a substituent in the "optionally substituted amino" represented by $R^1$ includes a $C_{1-6}$ alkyl such as methyl, ethyl, propyl, isopropyl, butyl, isobutyl, sec-butyl, tert-butyl, pentyl, hexyl, etc.

In the "optionally substituted alkyl," examples of the substituent are the same as the substituent in the "optionally substituted alkylcarbonyl" as the acyl represented by $R^1$, with the same number of substituents.

The alkenyl in the "optionally substituted alkenyl" as a substituent in the "optionally substituted amino" represented by $R^1$ includes a $C_{2-6}$ alkenyl such as vinyl, propenyl, isopropenyl, 2-buten-1-yl, 4-penten-1-yl, 5-hexen-1-yl, etc.

In the "optionally substituted alkenyl," examples of the substituent are the same as the substituent in the "optionally substituted alkylcarbonyl" as the acyl represented by $R^1$, with the same number of substituents.

The alkynyl in the "optionally substituted alkynyl" as a substituent in the "optionally substituted amino" represented by $R^1$ includes a $C_{2-6}$ alkynyl such as 2-butyn-1-yl, 4-pentyn-1-yl, 5-hexyn-1-yl, etc.

In the "optionally substituted alkynyl," examples of the substituent are the same as the substituent in the "optionally substituted alkylcarbonyl" as the acyl represented by $R^1$, with the same number of substituents.

The cycloalkyl in the "optionally substituted cycloalkyl" as a substituent in the "optionally substituted amino" represented by $R^1$ includes a $C_{3-8}$ cycloalkyl such as cyclopropyl, cyclobutyl, cyclopentyl, cyclohexyl, cycloheptyl, cyclooctyl, etc.

In the "optionally substituted cycloalkyl," examples of the substituent are the same as the substituent in the "optionally substituted alkylcarbonyl" as the acyl represented by $R^1$, with the same number of substituents.

The aryl in the "optionally substituted aryl" as a substituent in the "optionally substituted amino" represented by $R^1$ includes a $C_{6-14}$ aryl such as phenyl, 1-naphthyl, 2-naphthyl, 2-biphenylyl, 3-biphenylyl, 4-biphenylyl, 2-anthryl, etc.

In the "optionally substituted aryl," examples of the substituent are the same as the substituent in the "optionally substituted alkylcarbonyl" as the acyl represented by $R^1$, with the same number of substituents.

The aralkyl in the "optionally substituted aralkyl" as a substituent in the "optionally substituted amino" represented by $R^1$ includes a $C_{7-16}$ aralkyl such as benzylthio, phenethylthio, etc.

In the "optionally substituted aralkyl," examples of the substituent are the same as the substituent in the "optionally substituted alkylcarbonyl" as the acyl represented by $R^1$, with the same number of substituents.

The heterocyclic group in the "optionally substituted heterocyclic group" as a substituent in the "optionally substituted amino" represented by $R^1$ includes a 5- to 14-membered heterocyclic group containing 1 to 4 hetero atoms, which are 1 or 2 different atoms selected from nitrogen, sulfur and oxygen atoms, in addition to carbon atoms (e.g., an aromatic heterocyclic group such as 2-thienyl, 3-thienyl, 2-furyl, 3-furyl, 2-pyridyl, 3-pyridyl, 4-pyridyl, 2-quinolyl, 3-quinolyl, 4-quinolyl, 5-quinolyl, 8-quinolyl, 1-isoquinolyl, 3-isoquinolyl, 4-isoquinolyl, 5-isoquinolyl, pyrazinyl, 2-pyrimidinyl, 4-pyrimidinyl, 3-pyrrolyl, 2-imidazolyl, 3-pyridazinyl, 3-isothiazolyl, 3-isooxazolyl, 1-indolyl, 2-indolyl, 3-indolyl, 2-benzothiazolyl, 2-benzo[b]thienyl, 3-benzo[b]thienyl, 2-benzo[b]furanyl, 3-benzo[b]furanyl, etc.; a non-aromatic heterocyclic group such as 2-pyrrolidinyl, 3-pyrrolidinyl, 2-imidazolinyl, 4-imidazolinyl, 3-pyrazolidinyl, 4-pyrazolidinyl, 2-piperidyl, 3-piperidyl, 4-piperidyl, 2-piperazinyl, etc.).

In the "optionally substituted heterocyclic group," examples of the substituent are the same as the substituent in the "optionally substituted alkylcarbonyl" as the acyl represented by $R^1$, with the same number of substituents.

The "optionally substituted alkylcarbonyl," "optionally substituted alkenylcarbonyl," "optionally substituted alkynylcarbonyl," "optionally substituted cycloalkylcarbonyl," "optionally substituted arylcarbonyl," "optionally substituted aralkylcarbonyl" and "optionally substituted heterocyclic carbonyl" as substituents in the "optionally substituted amino" represented by $R^1$ are those in the "optionally substituted alkylcarbonyl," "optionally substituted alkenylcarbonyl," "optionally substituted alkynylcarbonyl," "optionally substituted cycloalkylcarbonyl," "optionally substituted arylcarbonyl," "optionally substituted aralkylcarbonyl" and "optionally substituted heterocyclic carbonyl" shown as the acyl groups represented by $R^1$ described above.

In Compound (I), $R^2$ represents an optionally substituted branched alkyl, an optionally substituted cycloalkyl, an optionally substituted fused homocyclic group, or represented by formula:

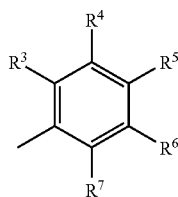

(wherein, $R^3$ and $R^7$ each independently represents (i) hydrogen atom, (ii) fluorine atom, (iii) bromine atom, (iv) nitro, (v) cyano, (vi) an optionally substituted alkyl, (vii) an optionally substituted alkoxy (viii) an optionally substituted aryl, (ix) an acyl, (x) an optionally substituted alkylsulfonyl (xi) an optionally substituted carbamoyl or (xii) an optionally substituted amino; $R^4$ and $R^6$ each independently represents (i) hydrogen atom, (ii) fluorine atom, (iii) bromine atom, (iv) hydroxy (v) cyano, (vi) an alkyl having a substituent selected from carboxy, a halogen atom, an alkoxycarbonyl and an arylcarbonylamino, (vii) an optionally substituted alkoxy, (viii) an optionally substituted aryl, (ix) an acyl, (x) an optionally substituted alkylsulfonyl, (xi) an optionally substituted carbamoyl, (xii) an optionally substituted amino or (xiii) an optionally substituted alkoxycarbonyl; and $R^5$ represents (i) hydrogen atom, (ii) fluorine atom, (iii) hydroxy (iv) cyano, (v) an alkyl substituted with a halogen atom, (vi) an optionally substituted aryl, (vii) an acyl, (viii) an optionally substituted carbamoyl or (ix) an optionally substituted amino (provided that the compounds wherein all of $R^3$ to $R^7$ represent hydrogen atoms are excluded)).

The branched alkyl in the "optionally substituted branched alkyl" represented by $R^2$ includes a branched $C_{3-6}$ alkyl such as isopropyl, isobutyl, sec-butyl, tert-butyl, etc.

In the "optionally substituted branched alkyl," examples of the substituent are the same as the substituent in the "optionally substituted alkylcarbonyl" as the acyl represented by $R^1$, with the same number of substituents.

The cycloalkyl in the "optionally substituted cycloalkyl" represented by $R^2$ includes a $C_{3-8}$ cycloalkyl such as cyclopropyl, cyclobutyl, cyclopentyl, cyclohexyl, cycloheptyl, cyclooctyl, etc.

In the "optionally substituted cycloalkyl," examples of the substituent are the same as the substituent in the "optionally substituted alkylcarbonyl" as the acyl represented by $R^1$, with the same number of substituents.

The condensed homocyclic group in the "optionally substituted fused homocyclic group" represented by $R^2$ includes a $C_{9-14}$ condensed homocyclic group such as 1-indenyl, 2-indenyl, 3-indenyl, 4-indenyl, 5-indenyl, 6-indenyl, 7-indenyl, 1-indanyl, 2-indanyl, 4-indanyl, 5-indanyl, 3-indenyl, 1-naphthyl, 2-naphthyl, 1,2,3,4-tetrahydro-1-naphthyl, 1,2,3, 4-tetrahydro-2-naphthyl, 1,2,3,4-tetrahydro-5-naphthyl, 1,2, 3,4-tetrahydro-6-naphthyl, etc.

In the "optionally substituted condensed homocyclic group," examples of the substituent are the same as the substituent in the "optionally substituted alkylcarbonyl" as the acyl represented by $R^1$, with the same number of substituents.

The alkyl in the "optionally substituted alkyl" represented by $R^3$ and $R^7$ includes a $C_{1-6}$ alkyl such as methyl, ethyl, propyl, isopropyl, butyl, isobutyl, sec-butyl, tert-butyl, pentyl, hexyl, etc.

In the "optionally substituted alkyl," examples of the substituent are the same as the substituent in the "optionally substituted alkylcarbonyl" as the acyl represented by $R^1$, with the same number of substituents.

The alkoxy in the "optionally substituted alkoxy" represented by $R^3$, $R^4$, $R^6$ and $R^7$ includes a $C_{1-6}$ alkoxy such as methoxy, ethoxy, propoxy, isopropoxy, butoxy, isobutoxy, sec-butoxy, tert-butoxy, pentyloxy, hexyloxy, etc.

In the "optionally substituted alkoxy," examples of the substituent are the same as the substituent in the "optionally substituted alkylcarbonyl" as the acyl represented by $R^1$, with the same number of substituents.

The aryl in the "optionally substituted aryl" represented by $R^3$, $R^4$, $R^5$, $R^6$ and $R^7$ includes a $C_{6-14}$ aryl such as phenyl, 1-naphthyl, 2-naphthyl, 2-biphenylyl, 3-biphenylyl, 4-biphenylyl, 2-anthryl, etc.

In the "optionally substituted aryl," examples of the substituent are the same as the substituent in the "optionally substituted alkylcarbonyl" as the acyl represented by $R^1$, with the same number of substituents.

The "acyl" represented by $R^3$, $R^4$, $R^5$, $R^6$ and $R^7$ includes the same examples as in the "acyl" above represented by $R^1$.

The alkylsulfonyl in the "optionally substituted alkylsulfonyl" represented by $R^3$, $R^4$, $R^6$ and $R^7$ includes a $C_{1-6}$ alkylsulfonyl such as methylsulfonyl, ethylsulfonyl, propylsulfonyl, isopropylsulfonyl, butylsulfonyl, isobutylsulfonyl, sec-butylsulfonyl, tert-butylsulfonyl, pentylsulfonyl, hexylsulfonyl, etc.

In the "optionally substituted alkylsulfonyl," examples of the substituent are the same as the substituent in the "optionally substituted alkylcarbonyl" as the acyl represented by $R^1$, with the same number of substituents.

The carbamoyl in the "optionally substituted carbamoyl" represented by $R^3$, $R^4$, $R^5$, $R^6$ and $R^7$ includes, for example, a group formed by combining carbonyl with an optionally substituted amino.

The "optionally substituted amino" includes the same examples as in the "optionally substituted amino" represented by $R^1$ and described above.

The "optionally substituted amino" represented by $R^3$, $R^4$, $R^5$, $R^6$ and $R^7$ includes the same examples as in the "optionally substituted amino" represented by $R^1$ and described above.

The "alkyl having a substituent selected from carboxy, a halogen atom, an alkoxycarbonyl and an arylcarbonylamino" represented by $R^4$ and $R^6$ includes a $C_{1-6}$ alkyl having 1 to 3 substituents selected from, e.g., carboxy, fluorine atom, chlorine atom, bromine atom, iodine atom, a $C_{1-6}$ alkoxy-carbonyl (e.g., methoxycarbonyl, ethoxycarbonyl, propoxycarbonyl, isopropoxycarbonyl, butoxycarbonyl, isobutoxycarbonyl, sec-butoxycarbonyl, tert-butoxycarbonyl, pentyloxycarbonyl, hexyloxycarbonyl, etc.) and a $C_{6-14}$ aryl-carbonylamino (e.g., benzoylamino, naphthoylamino, etc.), etc.

The alkoxycarbonyl in the "optionally substituted alkoxycarbonyl" represented by $R^4$ and $R^6$ includes a $C_{1-6}$ an alkoxycarbonyl such as methoxycarbonyl, ethoxycarbonyl, propoxycarbonyl, isopropoxycarbonyl, butoxycarbonyl, isobutoxycarbonyl, sec-butoxycarbonyl, tert-butoxycarbonyl, pentyloxycarbonyl, hexyloxycarbonyl, etc.

In the "optionally substituted alkoxycarbonyl," examples of the substituent are the same as the substituent in the "optionally substituted alkylcarbonyl" as the acyl represented by $R^1$, with the same number of substituents.

The "alkyl substituted with a halogen atom" represented by $R^5$ includes a $C_{1-6}$ alkyl (e.g., methyl, ethyl, propyl, isopropyl, butyl, isobutyl, sec-butyl, tert-butyl, pentyl, hexyl, etc.) having 1 to 5 (preferably 1 to 3) halogens including fluorine, chlorine, bromine and iodine. Specific examples are chloromethyl, dichloromethyl, trichloromethyl, bromomethyl, fluoromethyl, difluoromethyl, trifluoromethyl, 2,2,2-trifluoroethyl, 1,1,2,2,2-pentafluoroethyl, etc.

In Compound (I), n represents an integer of 0 to 4. Inter alia, n is preferably 0.

Preferably, $R^1$ represents (1) hydrogen atom, (2) a halogen atom and (3) an optionally halogenated $C_{1-6}$ alkyl, etc. Hydrogen atom is particularly preferred.

Preferably, $R^2$ represents (1) an optionally substituted branched alkyl, (2) an optionally substituted cycloalkyl and a group represented by formula:

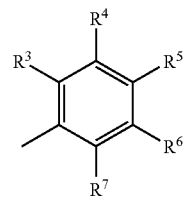

(wherein each symbol has the same significance as described above), more preferably, (1) a branched $C_{3-6}$ alkyl, (2) a $C_{3-8}$ cycloalkyl and (3) a group represented by formula:

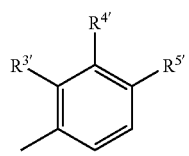

(wherein, $R^{3'}$ represents (1') hydrogen atom, (2') a $C_{1-6}$ alkoxy or (3) a $C_{1-6}$ alkyl substituted with 1 to 5 halogen atoms; $R^{4'}$ represents (1) hydrogen atom, (2) bromine atom, (3) cyano, (4) a $C_{1-6}$ alkyl having 1 to 3 substituents selected from carboxy, a halogen atom, a $C_{1-6}$ alkoxy-carbonyl and a $C_{6-14}$ aryl-carbonylamino (5) a $C_{1-6}$ alkoxy substituted with a $C_{1-6}$ alkoxy-carbonyl or (6) a $C_{1-6}$ alkyl-carbonylamino; and $R^{5'}$ represents hydrogen atom, hydroxy, cyano, a $C_{1-6}$ alkyl substituted with 1 to 5 halogen atoms, a $C_{6-14}$ aryl, a $C_{1-6}$ alkyl-carbonyl, a di-$C_{1-6}$alkyl-carbamoyl or a $C_{1-6}$ alkyl-carbonylamino). Among them, (1) $C_{3-8}$ cycloalkyl and (2) a group represented by formula:

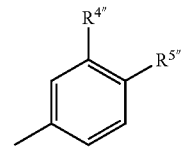

(wherein, $R^{4''}$ represents hydrogen atom or cyano, and $R^{5''}$ represents hydrogen atom, a $C_{1-6}$ alkyl-carbonyl or a $C_{1-6}$ alkyl-carbonylamino) are preferred, more preferably, a group represented by formula:

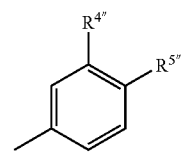

(wherein $R^{4''}$ represents hydrogen atom or cyano, and $R^{5''}$ represents hydrogen atom, a $C_{1-6}$ alkyl-carbonyl or a $C_{1-6}$ alkyl-carbonylamino).

Preferred examples of Compound (I) include
2-(3-cyanophenyl)-4H-1,3-benzothiazin-4-one,
2-(4-acetylphenyl)-4H-1,3-benzothiazin-4-one,
2-(4-methylsulfonylphenyl)-4H-1,3-benzothiazin-4-one,
2-(4-acetylaminophenyl)-4H-1,3-benzothiazin-4-one, 2-(3-trifluoromethylphenyl)-4H-1,3-benzothiazin-4-one, or salts thereof, etc.

As salts of Compound (I), there are, for example, metal salts, ammonium salts, salts with organic bases, salts with inorganic acids, salts with organic acids, salts with basic or acidic amino acids, etc. Preferred examples of the metal salts include alkali metal salts such as sodium salts, potassium salts; alkaline earth metal salts such as calcium salts, magnesium salts, barium salts, etc.; aluminum salts, and the like. Preferred examples of the salts with organic bases include salts with trimethylamine, triethylamine, pyridine, picoline, 2,6-lutidine, ethanolamine, diethanolamine, triethanolamine, dicyclohexylamine, N,N'-dibenzylethylenediamine, etc. Preferred examples of the salts with inorganic acids include salts with hydrochloric acid, hydrobromic acid, nitric acid, sulfuric acid, phosphoric acid, etc. Preferred examples of the salts with organic acids include salts with formic acid, acetic acid, trifluoroacetic acid, phthalic acid, fumaric acid, oxalic acid, tartaric acid, maleic acid, citric acid, succinic acid, malic acid, methanesulfonic acid, benzenesulfonic acid, p-toluenesulfonic acid, etc. Preferred examples of the salts with basic amino acids include salts with arginine, lysine, ornithine, etc. Preferred examples of the salts with acidic amino acids include salts with aspartic acid, glutamic acid, etc.

Among them, preferred are pharmaceutically acceptable salts. For example, where the compounds have acidic functional groups therein, inorganic salts such as alkali metal salts (e.g., sodium salts, potassium salts, etc.), alkaline earth metal salts (e.g., calcium salts, magnesium salts, barium salts, etc.), ammonium salts, etc. are preferred; where the compounds have basic functional groups therein, preferred are salts with hydrobromic acid, nitric acid, sulfuric acid, phosphoric acid, etc., or salts with organic acids such as acetic acid, phthalic acid, fumaric acid, oxalic acid, tartaric acid, maleic acid, citric acid, succinic acid, methanesulfonic acid, p-toluenesulfonic acid, etc.

Compound (I) may be any of hydrates and non-hydrates. Examples of the hydrates are 0.5 hydrate, 1 hydrate, 1.5 hydrate and 2 hydrate, etc.

When $R^2$ in Compound (I) represents the optionally substituted branched alkyl or optionally substituted cycloalkyl, the compound may have a resonance structure.

Where Compound (I) is obtained as a mixture of optically active substances (racemates), the mixture can be resolved into the desired (R)- and (S)-forms by means of publicly known optical resolution.

Compound (I) may be labeled with an isotope (e.g., $^3H$, $^{14}C$, $^{35}S$), etc.

The prodrug of Compound (I) is used to mean a compound that is converted into Compound (I) upon interaction with enzymes or gastric juice, etc. under physiological conditions in the body, namely, a compound that is converted into Compound (I) upon enzymatic oxidation, reduction, hydrolysis, etc., or a compound that is converted into Compound (I) upon hydrolysis, etc. by gastric juice, etc. The prodrugs of Compound (I) include compounds wherein an amino of Compound (I) is acylated, alkylated or phosphorylated [e.g., the amino in Compound (I) is substituted with eicosanoyl, alanyl, pentylaminocarbonyl, (5-methyl-2-oxo-1,3-dioxolen-4-yl)-methoxycarbonyl, tetrahydrofuranyl, pyrrolidylmethyl, pivaloyloxymethyl, tert-butyl, etc.], compounds wherein a hydroxy of Compound (I) is acylated, alkylated, phosphorylated, borated, etc. [e.g., compounds wherein a hydroxy of Compound (I) is substituted with acetyl, palmitoyl, propanoyl, pivaloyl, succinyl, fumaryl, alanyl, dimethylaminomethylcarbonyl, etc.], or compounds wherein a carboxy in Compound (I) is esterified or amidated [compounds wherein a carboxy in Compound (I) is substituted with ethyl, phenyl, carboxymethyl, dimethylaminomethyl, pivaloyloxymethyl, ethoxycarbonyloxyethyl, phthalidyl, (5-methyl-2-oxo-1,3-dioxolen-4-yl)methyl, cyclohexyloxycarbonylethyl, methylamide, etc.], and so on. These compounds can be manufactured by per se known methods from Compound (I).

The prodrug of Compound (I) may be a compound which is converted into Compound (I) under the physiological conditions as described in "Pharmaceutical Research and Development", vol. 7, Drug Design, pages 163-198 published 1990 by Hirokawa Publishing Co.

Processes for producing Compound (I) are described below

Compound (I) can be produced by Processes 1 and 2 shown by the following schemes, or by modifications of these processes, etc. Compounds described in the following schemes include their salts. For their salts, there are, for example, the same salts as those of compound (I), etc.

Process 1:

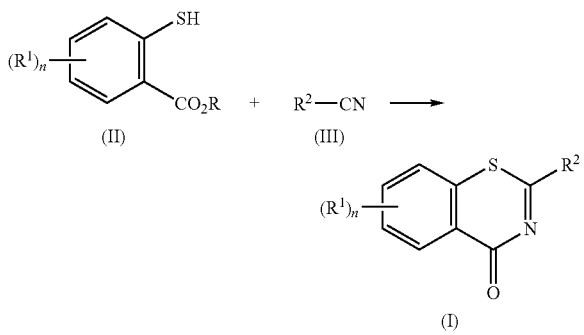

[wherein R represents hydrogen atom or an alkyl (preferably, a $C_{1-6}$ alkyl such as methyl, ethyl, etc.) and the remaining symbols have the same significance as described above].

Compound (I) can be produced by reacting Compound (II) with Compound (III) in the presence of a base.

Compound (III) is used in an amount of approximately 0.4 to 2.0 mol, preferably approximately 0.8 to 1.2 mol, based on 1 mol of Compound (II). The base is used in an amount of approximately 1 to 2.5 mol, preferably approximately 1 to 1.5 mol, based on 1 mol of Compound (II). Examples of the "base" include basic salts such as sodium carbonate, potassium carbonate, cesium carbonate, etc.; inorganic bases such as sodium hydroxide, potassium hydroxide, etc.; aromatic amines such as pyridine, lutidine, etc.; tertiary amines such as triethylamine, tripropylamine, tributylamine, cyclohexyldimethylamine, 4-dimethylaminopyridine, N,N-dimethylaniline, N-methylpiperidine, N-methylpyrrolidine, N-methylmorpholine, etc.; alkali metal hydrides such as sodium hydride, potassium hydride, etc.; metal amides such as sodium amide, lithium diisopropylamide, lithium hexamethyldisilazide, etc.; metal alkoxides such as sodium methoxide, sodium ethoxide, potassium tert-butoxide, etc.

Advantageously, the reaction is carried out in the absence of any solvent or in the presence of a solvent inert to the reaction. The solvent is not particularly limited so far as the reaction proceeds, but examples of the solvent used are aromatic amines, halogenated hydrocarbons, aliphatic hydrocarbons, aromatic hydrocarbons, ethers, amides or a mixture of two or more of these solvents, etc. Among them, pyridine, toluene, etc. are preferred. When the reaction is carried out in, e.g., pyridine, the base is not necessarily required.

The reaction temperature may be normally about 100 to 150° C., preferably 110 to 120° C. When the reaction is carried out at the boiling point of a solvent used, the reaction time may be usually about 3 to 72 hours, preferably about 8 to 24 hours.

Preferably, the reaction is carried out under reflux at the boiling point of a solvent used.

Where Compound (II) is commercially available, it can be used as it is; alternatively, Compound (II) may be produced by per se known methods or their modifications. For example, the desired compound (II) can be produced from anthranylic acids corresponding to Compound (II) by publicly known processes (e.g., Journal of Organic Chemistry, 18, 1380, 1953, etc.) or from salicylic acids corresponding to Compound (II) by publicly known processes (e.g., Journal of Organic Chemistry, 31, 3980, 1966, etc.).

Where Compound (III) is commercially available, it can be used as it is; alternatively, Compound (III) may be produced by per se known methods or their modifications.

Process 2:

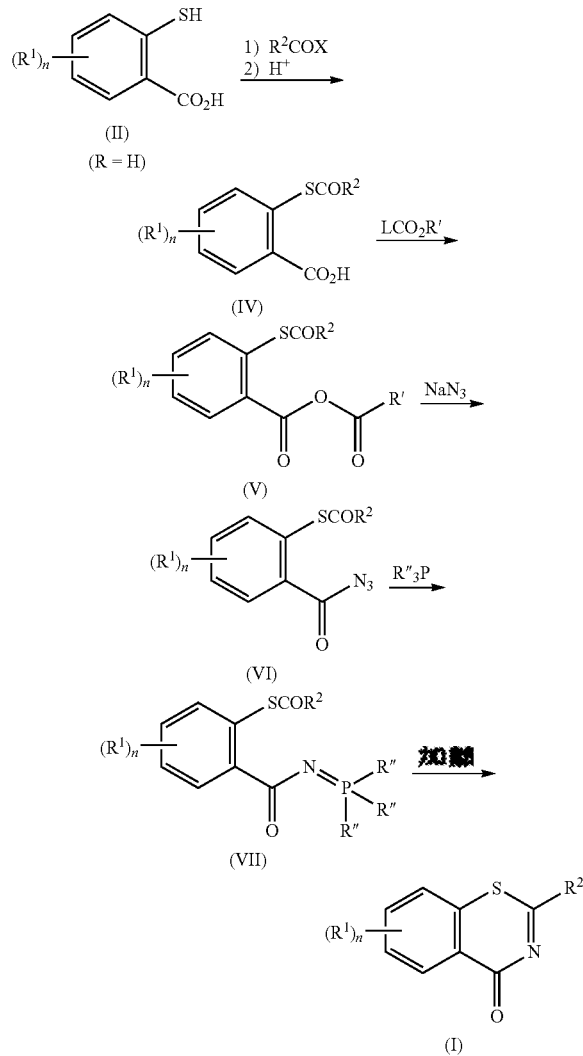

[wherein X is a halogen atom and $R^2$ is a group represented by $CO_2$—, etc.; the leaving group L represents a halogen atom, etc.; the leaving group $R^1$ is an alkyl (preferably, a $C_{1-6}$ alkyl such as methyl, ethyl, etc.); R" is an alkyl (preferably, a $C_{1-6}$ alkyl such as methyl, ethyl, etc.) or an aryl (preferably, a $C_{6-10}$ aryl such as phenyl, etc.); and the remaining symbols have the same significance as described above].

Compound (I) can be produced by a modification of the process described in Chem. Ber., 118, 4632-4636, 1985.

Production of Compound (IV):

The reaction may be carried out in the presence of a base.

The acylating agent represented by $R^2COX$ is used in an amount of about 1.0 to 2.0 mol, preferably about 1.0 to 1.5 mol, based on 1 mol of Compound (II).

The base is used in an amount of about 2.0 to 3.0 mol, preferably about 2.2 to 2.5 mol, based on 1 mol of Compound (II). Examples of the "base" include basic salts such as sodium carbonate, potassium carbonate, cesium carbonate, etc.; inorganic bases such as sodium hydroxide, potassium hydroxide, etc.; aromatic amines such as pyridine, lutidine, etc.; tertiary amines such as triethylamine, tripropylamine, tributylamine, cyclohexyldimethylamine, 4-dimethylaminopyridine, N,N-dimethylaniline, N-methylpiperidine, N-methylpyrrolidine, N-methylmorpholine, etc.; alkali metal hydrides such as sodium hydride, potassium hydride, etc.; metal amides such as sodium amide, lithium diisopropylamide, lithium hexamethyldisilazide, etc.; metal alkoxides such as sodium methoxide, sodium ethoxide, potassium tert-butoxide, etc.

Advantageously, the reaction is carried out in the absence of any solvent or in the presence of a solvent inert to the reaction. The solvent is not particularly limited so far as the reaction proceeds, but examples of the solvent used are aromatic amines, halogenated hydrocarbons, aliphatic hydrocarbons, aromatic hydrocarbons, ethers, amides or a mixture of two or more of these solvents, etc.

The reaction temperature may be normally about −5° C. to 50° C., preferably −5° C. to 110° C. The reaction time may be about 0.5 to 4 hours, preferably about 0.5 to 1 hour.

Production of Compound (V):

The reaction may be carried out in the presence of a base.

The halogenoformic acid ester represented by $LCO_2R'$ is used in an amount of about 1.0 to 2.0 mol, preferably about 1.0 to 1.5 mol, based on 1 mol of Compound (IV).

The base is used in an amount of about 1 to 2.5 mol, preferably about 1 to 1.5 mol, based on 1 mol of Compound (II). Examples of the "base" include basic salts such as sodium carbonate, potassium carbonate, cesium carbonate, etc.; inorganic bases such as sodium hydroxide, potassium hydroxide, etc.; aromatic amines such as pyridine, lutidine, etc.; tertiary amines such as triethylamine, tripropylamine, tributylamine, cyclohexyldimethylamine, 4-dimethylaminopyridine, N,N-dimethylaniline, N-methylpiperidine, N-methylpyrrolidine, N-methylmorpholine, etc.; alkali metal hydrides such as sodium hydride, potassium hydride, etc.; metal amides such as sodium amide, lithium diisopropylamide, lithium hexamethyldisilazide, etc.; metal alkoxides such as sodium methoxide, sodium ethoxide, potassium tert-butoxide, etc.

Advantageously, the reaction is carried out in the absence of any solvent or in the presence of a solvent inert to the reaction. The solvent is not particularly limited so far as the reaction proceeds, but examples of the solvent used are aromatic amines, halogenated hydrocarbons, aliphatic hydrocarbons, aromatic hydrocarbons, ethers, amides or a mixture of two or more of these solvents, etc.

The reaction temperature may be normally about −5° C. to 50° C., preferably −5° C. to 10° C. The reaction time may be about 0.5 to 4 hours, preferably about 0.5 to 1 hour.

Production of Compound (VI):

Sodium azide is used in an amount of about 1.0 to 2.0 mol, preferably about 1.0 to 1.5 mol, based on 1 mol of Compound (V).

The reaction is carried out advantageously in an aqueous solvent. The solvent is not particularly limited as far as the reaction proceeds, but there are used, for example, water, alcohols or a mixture of two or more of these solvents.

The reaction temperature may be normally about −5° C. to 50° C., preferably −5° C. to 10° C. The reaction time may be about 0.5 to 4 hours, preferably about 0.5 to 1 hour.

Production of Compound (I):

The tertiary phosphine represented by $R''_3P$ is used in an amount of about 1.0 to 2.0 mol, preferably about 1.0 to 1.5 mol, based on 1 mol of Compound (VI).

Advantageously, the reaction is carried out in the absence of any solvent or in the presence of a solvent inert to the reaction. The solvent is not particularly limited so far as the reaction proceeds, but examples of the solvent used are aromatic amines, halogenated hydrocarbons, aliphatic hydrocarbons, aromatic hydrocarbons, ethers, amides or a mixture of two or more of these solvents, etc.

The reaction is carried out normally at about −20° C. to 0° C., preferably at −10° C., by adding the tertiary phosphine and refluxing the reaction solution at the boiling point of a solvent used for about 0.1 to 2 hours, preferably about 0.1 to 0.5 hours.

In the reaction described above, where the starting compound contains amino, carboxy and hydroxy as the substituents, these groups may be protected by protecting groups generally used in peptide chemistry, etc., and the objective compound can be obtained, if necessary, by removing these protecting groups after the reaction.

As protecting groups for the amino, there are used, for example, formyl or an optionally substituted $C_{1-6}$ alkyl-carbonyl (e.g., acetyl, propionyl, etc.), phenylcarbonyl, a $C_{1-6}$ alkoxy-carbonyl (e.g., methoxycarbonyl, ethoxycarbonyl, etc.), phenyloxycarbonyl, a $C_{7-10}$ aralkyloxy-carbonyl (e.g., benzyloxycarbonyl, etc.), trityl or phthaloyl, etc. As the substituents for these groups, there are used a halogen atom (e.g., fluorine, chlorine, bromine, iodine, etc.), a $C_{1-6}$ alkyl-carbonyl (e.g., acetyl, propionyl, valeryl, etc.), nitro, etc. The number of substituents is 1 to 3.

As protecting groups for the carboxy, there are used, for example, an optionally substituted $C_{1-6}$ alkyl (e.g., methyl, ethyl, propyl, isopropyl, butyl, tert-butyl, 2-trimethyl, etc.), phenyl, trityl or silyl, etc. As the substituents for these groups, there are used a halogen atom (e.g., fluorine, chlorine, bromine, iodine, etc.), formyl, $C_{1-6}$ alkyl-carbonyl (e.g., acetyl, propionyl, butylcarbonyl, etc.), nitro, a $C_{1-6}$ alkyl (e.g., methyl, ethyl, tert-butyl, etc.), a $C_{6-10}$ aryl (e.g., phenyl, naphthyl, etc.), etc. The number of substituents is 1 to 3.

As protecting groups for the hydroxy, there are used, for example, an optionally substituted $C_{1-6}$ alkyl (e.g., methyl, ethyl, propyl, isopropyl, butyl, tert-butyl, etc.), phenyl, a $C_{7-11}$ aralkyl (e.g., benzyl, etc.), formyl, a $C_{1-6}$ alkyl-carbonyl (e.g., acetyl, propionyl, etc.), phenyloxycarbonyl, a $C_{7-11}$ aralkyloxy-carbonyl (e.g., benzyloxycarbonyl, etc.), tetrahydropyranyl, tetrahydrofuranyl or silyl, etc. As the substituents for these groups, there are used a halogen atom (e.g., fluorine, chlorine, bromine, iodine, etc.), a $C_{1-6}$ alkyl (e.g., methyl, ethyl, tert-butyl, etc.), a $C_{7-11}$ aralkyl (e.g., benzyl, etc.), a $C_{6-10}$ aryl (e.g., phenyl, naphthyl, etc.), nitro, etc. The number of substituents is 1 to 4.

To remove the protecting groups, per se known methods or their modifications are used. A method for removing the protective group may be a per se known method or a method analogous thereto, such as a treatment with an acid, a base, ultraviolet, hydrazine, phenylhydrazine, sodium N-methyldithiocarbamate, tetrabutylammonium fluoride, palladium acetate and the like as well as a reducing reaction.

In any method, publicly known deprotecting reactions, acylation, alkylation, hydrogenation, oxidization, reduction, carbon chain elongation and substituent-exchanging reaction may be employed singly or in combination of two or more to synthesize Compound (I). These reactions may be found in, e.g., SHIN-JIKKENKAGAKU-KOZA, Vols. 14 and 15, 1977 (MARUZEN Publishing Co.).

Examples of the "aromatic amines" described above are pyridine, lutidine, quinoline, etc.

Examples of the "halogenated hydrocarbons" described above are dichloromethane, chloroform, 1,2-dichloroethane, carbon tetrachloride, etc.

Examples of the "aliphatic hydrocarbons" described above are hexane, pentane, cyclohexane, etc.

Examples of the "aromatic hydrocarbons" described above are benzene, toluene, xylene, chlorobenzene, etc.

Examples of the "ethers" described above are diethyl ether, diisopropyl ether, diphenyl ether, tetrahydrofuran, dioxane, 1,2-dimethoxyethane, etc.

Examples of the "amides" described above are N,N-dimethylformamide, N,N-dimethylacetamide, hexamethylphosphoric triamide, etc.

Examples of the "alcohols" described above are methanol, ethanol, propanol, isopropanol, butanol, etc.

The desired product yielded by the reaction described above in a free form may be converted into a salt in a conventional manner. Alternatively, in case that the product yielded in a salt form may be converted into a free form or other salt in a conventional manner. Compound (I) thus obtained is isolated and purified from the reaction solution by known means such as partition, concentration, solvent extraction, fractional distillation, crystallization, recrystallization, chromatography, and the like.

When Compound (I) exists as a configurational isomer, diastereomer or conformer, each can be isolated, if necessary, by any of the isolation or separation means described above. When Compound (I) is a racemate, it can be separated into (S) and (R) forms, using a conventional means of optical resolution.

Where stereoisomers of compound (I) exist, these isomers, either alone or in a mixture thereof, are within the scope of the present invention.

Compound (I) of the present invention possesses an excellent cell death inhibitory activity (e.g., apoptosis inhibitory activity, cardiomyocyte apoptosis inhibitory activity, etc.) on animals, especially mammals (e.g., human, monkey, dog, cat, rabbit, guinea pig, rat, mouse, etc.) and has low toxicity (e.g., acute toxicity, chronic toxicity, genetic toxicity, reproductive toxicity, cardiotoxicity, drug-drug interaction and carcinogenesis). Furthermore, Compound (I) of the present invention is capable of binding to a macrophage migration inhibitory factor (MIF) and inhibits, for example, oxidative stress-induced cell death, serum-deprived cell death, cell death induced by growth factor deficiency, cell death induced by HMG-CoA reductase inhibitor, cell death induced by anti-cancer agents, NO-mediated cell death, cell death induced by amyloid β protein, etc. For example, apoptosis induced in cardiomyocytes by various factors is observed as a loss of cardiomyocytes from the myocardium, which adversely affects the heart function. Thus, the compound having the myocardial cell death inhibitory activity can prevent from the occurring adverse effect on the heart function due to a loss of cardiomyocytes. Moreover, Compound (I) of the present invention has a tumor growth inhibitory action, an angiogenesis inhibitory action, etc.

In addition, the substance capable of binding to MIF has an activity of promoting the expression of genes under control of antioxidant response element (ARE)(e.g., genes of factors for protecting cells from various stresses; etc.), an activity of enhancing (promoting) the production of gene proteins (gene products) under control of ARE, or an activity of promoting their activities; and the like.

As the genes under control of ARE, there are heme oxygenase-1, liver glutathione S-transferase Ya subunit, liver glutathione S-transferase Yc subunit, glutathione S-transferase Yb subunit, glutathione S-transferase Yc1 subunit, gamma-glutamylcysteine synthetase, NAD(P)H: quinone reductase, UDP-glucuronosyltransferase, exon 1, bilirunin-specific UDP-glucuronosyltransferase, NAD(P)H-menadione oxidereductase, etc.

As such, the compound capable of binding to MIF increases the factors for protecting cells from stress, thereby to strongly inhibit cell death induced by various factors.

Thus, Compound (I) is useful as a safe pharmaceutical and hence useful as an agent for preventing or treating, for instance, circulatory system diseases [for example, cardiomyopathy (e.g., congestive cardiomyopathy, hypertrophic obstructive cardiomyopathy, hypertrophic cardiomyopathy, idiopathic cardiomyopathy, constrictive cardiomyopathy, diabetic cardiomyopathy, etc.), heart failure (e.g., chronic heart failure, chronic congestive heart failure, acute heart failure, cardiac decompensation, left cardiac failure, right heart failure, congestive heart failure, acute congestive heart failure, metabolic heart failure, congestive heart failure, high output heart failure, low output heart failure, intractable heart failure, adverse prognosis of myocardial infarction, etc., angina pectoris, myocardial infarction, etc.], neurodegenerative diseases [e.g., Parkinson's disease, Alzheimer's disease, triplet repeat disease (e.g., Huntington's chorea, spinocerebellar ataxia 1, Machado-Joseph disease, dentatorubral-pallidoluysian atrophy, etc.), prion disease (e.g., Creutzfeldt-Jakob disease, mad cow disease, etc.), amyotrophic lateral sclerosis (ALS), cerebellar degeneration, retinitis pigmentosa, etc.], cerebrovascular diseases (e.g., cerebral infarction, etc.), central nervous infections (e.g., HIV encephalitis, bacterial meningitis, etc.), traumatic diseases (e.g., spinal cord injury, brain injury, etc.), demyelinating diseases (e.g., multiple sclerosis, etc.), bone/joint diseases (e.g., osteoporosis, arthritis deformans, rheumatism, etc.), kidney diseases (e.g., ischemic acute renal failure, hemolytic uremic syndrome, acute tubular necrosis, hydronephrosis, glomerulonephritis, diabetic nephropathy, graft rejected kidney, etc.), liver diseases (e.g., viral hepatitis, alcoholic hepatitis, etc.), myelodysplastic diseases (e.g., aplastic anemia, etc.), AIDS, arteriosclerosis, diabetes, pulmonary hypertension, sepsis, infectious diseases (e.g., immunodeficiency, pneumonia, influenza, etc.), inflammatory diseases (e.g., (1) diabetic complications such as fever by ache, retinopathy, nephropathy, neuropathy, etc., (2) arthritis such as chronic articular rheumatism, rheumatoid myelitis, gouty arthritis, periostitis, etc., (3) inflammatory bowel diseases such as ulcerative colitis, etc., (4) inflammatory pulmonary diseases such as pneumonia, silicosis, pulmonary sarcoidosis, pulmonary tuberculosis, etc., (5) backache, (6) gout, (7) neuralgia, (8) pharyngitis, (9) cystitis, (10) chronic hepatitis, (11) acute pancreatitis, (12) chronic pancreatitis, (13) Crohn's disease, (14) meningitis, (15) inflammatory oculopathy, etc.), autoimmune diseases (e.g., systemic lupus erythematosus, atopic dermatitis, etc.), failure accompanying rejection in organ transplantation, cancers (e.g., colon cancer, breast cancer, lung cancer, prostate cancer, esophageal cancer, gastric cancer, liver cancer, biliary tract cancer, spleen cancer, renal cancer, bladder cancer, uterine cancer, testicular cancer, thyroid cancer, pancreatic cancer, brain tumor, blood tumor, etc.), etc.

Where Compound (I) is used as the preventive and/or therapeutic agent described above, the compound can be administered either orally or parenterally according to publicly known methods. Compound (I) is thus mixed with pharmaceutically acceptable carriers and orally administered generally in the form of solid preparations such as tablets, capsules, granules, powders, etc., or parenterally, i.e., intravenously, subcutaneously, intramuscularly, etc. in the form of injections, suppositories, buccals or the like. The compound may also be administered sublingually, subcutaneously, intramuscularly, etc., in the form of sustained-release preparations such as buccals, microcapsules, etc.

The dose of Compound (I) may vary depending on subject to be administered, route of administration or conditions but is not particularly limited. For the treatment of, e.g., heart failure, the single dose for an adult is usually about 0.001 to 10 mg/kg, preferably about 0.001 to 0.2 mg/kg, more preferably about 0.001 to 0.02 mg/kg. The dose is usually divided and administered about 1 to 3 times per day.

Compound (I) is contained in the pharmaceutical composition of the present invention in an amount of about 0.01 to 100% by weight, based on the total weight of the pharmaceutical.

The pharmaceutically acceptable carriers described above include a wide variety of organic or inorganic carrier materials conventionally used for pharmaceutical preparations, and are formulated as, for example, excipients, lubricants, binders, disintegrators, solvents, dissolution aids, suspending agents, isotonizing agents, buffers, soothing agents, etc. If necessary, additives such as preservatives, antioxidants, coloring agents, sweeteners, etc. can also be used.

Preferred examples of the excipients described above include lactose, white sugar, D-mannitol, starch, crystalline cellulose, light silicic anhydride, etc. Preferred examples of the lubricants described above include magnesium stearate, calcium stearate, talc, colloidal silica, etc. Preferred examples of the binders described above include crystalline cellulose, white sugar, D-mannitol, dextrin, hydroxypropyl cellulose, hydroxypropylmethyl cellulose, polyvinyl pyrrolidone, etc. Preferred examples of the disintegrators described above include starch, carboxymethyl cellulose, calcium carboxymethyl cellulose, sodium croscarmellose, sodium carboxymethyl starch, etc. Preferred examples of the solvents described above include water for injection, alcohol, propylene glycol, Macrogol, sesame oil, corn oil, etc. Preferred examples of the dissolution aids described above include polyethylene glycol, propylene glycol, D-mannitol, benzyl benzoate, ethanol, trisaminomethane, cholesterol, triethanolamine, sodium carbonate, sodium citrate, etc. Preferred examples of the suspending agents described above include surfactants such as stearyl triethanolamine, sodium laurylsulfate, lauryl aminopropionate, lecithin, benzalkonium chloride, benzetonium chloride, glycerine monostearate; and hydrophilic polymers such as polyvinyl alcohol, polyvinyl pyrrolidone, sodium carboxymethyl cellulose, methyl cellulose, hydroxymethyl cellulose, hydroxyethyl cellulose, hydroxypropyl cellulose, etc. Preferred examples of the isotonizing agents described above include sodium chloride, glycerine, D-mannitol, etc. Preferred examples of the buffers described above include buffers such as phosphates, acetates, carbonates, citrates, etc. Preferred examples of the soothing agents described above include benzyl alcohol, etc. Preferred examples of the preservatives described above include para-oxybenzoic acid esters, chlorobutanol, benzyl alcohol, phenethyl alcohol, dehydroacetic acid, sorbic acid, etc. Preferred examples of the antioxidants described above include sulfites, ascorbic acid, etc.

By adding a suspending agent, a dissolution aid, a stabilizer, an isotonizing agent, a preservative etc., the compound of the present invention can be prepared as an intravenous, subcutaneous or intramuscular injection in a conventional manner. In such cases, Compound (I) of the present invention can be freeze-dried as necessary in a conventional manner. In administration to human, for example, the compound of the present invention can be safely administered orally or parenterally, directly as such or in the form of a pharmaceutical composition prepared by mixing the compound with a pharmacologically acceptable carrier, excipient and diluent chosen appropriately.

Such pharmaceutical compositions include oral preparations (e.g., powders, granules, capsules, tablets), injections, drip infusions, topical preparations (e.g., nasal preparations, transdermal preparations, etc.), suppositories (e.g., rectal suppositories, vaginal suppositories) and the like.

These preparations can be manufactured in a conventional manner generally used in pharmaceutical making processes.

An injection can be produced by dissolving, suspending or emulsifying Compound (I) together with a dispersing agent (e.g., Tween 80 (manufactured by Atlas Powder Company, USA), HCO 60 (manufactured by Nikko Chemicals Co., Ltd.), polyethylene glycol, carboxymethyl cellulose, sodium alginate, etc.), a preservative (e.g., methyl paraben, propyl paraben, benzyl alcohol, etc.), an isotonizing agent (e.g., sodium chloride, mannitol, sorbitol, glucose, etc.) and other additives to prepare an aqueous injection, or by dissolving, suspending or emulsifying in a vegetable oil such as olive oil, sesame oil, cottonseed oil, corn oil, etc., propylene glycol or the like to prepare an oily injection.

An oral preparation can be produced in a conventional manner by adding to Compound (I) an excipient (e.g., lactose, sucrose, starch, etc.), a disintegrant (e.g., starch, calcium carbonate, etc.), a binder (e.g., starch, gum arabic, carboxymethyl cellulose, polyvinylpyrrolidone, hydroxypropyl cellulose, etc.), a lubricant (e.g., talc, magnesium stearate, polyethylene glycol 6000, etc.) and other additives, compressing the resulting mixture and, if necessary, coating the compressed product for the purpose of taste masking, enteric degradation or sustained release by techniques per se publicly known. Coating agents for this purpose include, for example, hydroxypropylmethyl cellulose, ethyl cellulose, hydroxymethyl cellulose, hydroxypropyl cellulose, polyoxyethylene glycol, Tween 80, Prulonic F68, cellulose acetate phthalate, hydroxypropylmethyl cellulose phthalate, hydroxymethyl cellulose acetate succinate, Eudragit (manufactured by Rohm Company, Germany, methacrylic acid/acrylic acid copolymer) and dyes (e.g., iron oxide, titanium dioxide). In an enteric preparation, for the purpose of separation of the two phases an intermediate phase may be provided between the enteric phase and the drug-containing phase in a conventional manner.

A topical preparation can be prepared in a conventional manner by compounding Compound (I) or its salt as a solid, semi-solid or liquid composition. The solid composition described above is prepared by, for example, powdering Compound (I) or its salt as such or in a mixture with an excipient (e.g., glycol, mannitol, starch, microcrystalline cellulose, etc.), a thickening agent (e.g., natural rubber, cellulose derivatives, acrylic polymer, etc.) and other additives. The liquid composition described above is prepared into an oily or aqueous suspension in almost the same manner as with the injection. The semi-solid composition is preferably an aqueous or oily gel, or an ointment. All of these compositions may contain a pH regulator (e.g., carbonic acid, phosphoric acid, citric acid, hydrochloric acid, sodium hydroxide, etc.), a preservative (e.g., paraoxybenzoic acid esters, chlorobutanol, benzalkonium chloride, etc.) and other additives.

For example, in a suppository, Compound (I) is prepared into an oily or aqueous solid, semi-solid or liquid composition by techniques per se publicly known. Oily bases used for the composition described above include glycerides of higher fatty acids [e.g., cacao butter, uitepsols (manufactured by Dynamite Nobel Company, Germany), etc.], moderate fatty acids [e.g., MIGLYOL, manufactured by Dynamite Nobel Company, Germany), etc.], vegetable oils (e.g., sesame oil, soybean oil, cottonseed oil, etc.), and the like. Aqueous bases include, for example, polyethylene glycols and propylene glycol. Bases for aqueous gels include, for example, natural rubbers, cellulose derivatives, vinyl polymers, acrylic polymers, etc.

The other drugs to be used in combination with Compound (I) includes, for example, those given below. In this case, these drugs can be administered orally or parenterally (e.g., as nasal preparations, injections, suppositories preparations, etc.). Alternatively, these drugs may be formulated in a single preparation or may be mixed with pharmaceutically acceptable carriers, excipients, binders, diluents or the like, which can be administered individually or simultaneously. When these drugs are individually formulated in the respective preparations, the individual preparations may be administered by mixing them using e.g. a diluent when administered; or, each of the individual preparations may also be administered to the one and same subject, separately or simultaneously or with time intervals.

Examples of drugs which provide a synergistic effect by the combined use of Compound (I) include cardiotonic agents (e.g., cardiotonic glycosides such as digoxin, etc., β agonists such as dopamine, dobutamine, etc., phosphodiesterase inhibitors such as amrinone, milrinone, etc.); antiarrhythmic drugs (e.g., class I antiarrhythmic drugs such as disopyramide, lidocaine, procainamide, etc., class III antiarrhythmic drugs such as amiodarone, sotalol, etc., β blockers such as propranolol, etc.); vasodilators (e.g., angiotensin converting enzyme inhibitors such as captopril, enalapril, etc., nitrate drugs such as nitroprusside, sorbide dinitrate, etc., calcium receptor antagonists such as verapamil, diltiazem, nicardipine, nifedipine, etc., angiotensin II receptor antagonists such as losartan, candesartan, etc.; diuretic agents (e.g., loop diuretics such as furosemide, bumetamide, etc., thiazide diuretics such as chlorothiazide, bendrofluazide, etc., potassium-sparing diuretic agents such as amiloride, spironolactone, etc.) and the like.

Furthermore, when Compound (I) is used in combination with HMG-CoA reductase inhibitors (simvastatin, atorvastatin, etc.), fibrate-type antihyperlipidemic drugs (e.g., gemfibrozil, etc.), anticancer agents (e.g., ifosfamide, UFT, adriamycin, doxorubicin, peplomycin, cisplatin, cyclophosphamide, 5-FU, methotrexate, mitomycin C, mitoxantrone, etc.) or the like, side effects by the HMG-CoA reductase inhibitors, fibrate-type antihyperlipidemic drugs, anticancer agents, etc., which give damages to normal cells, are alleviated.

The sequence identification numbers in the sequence listing of the specification indicates the following sequence.

[SEQ ID NO: 1]

This shows the base sequence of ARE in rat glutathione S-transferase Ya subunit gene used in EXPERIMENT 2.

[SEQ ID NO: 2]

This shows the base sequence of mutant ARE in rat glutathione S-transferase Ya subunit gene used in EXPERIMENT 2.

The present invention is hereinafter described in more detail by referring to REFERENCE EXAMPLES, EXAMPLES, PREPARATION EXAMPLES and EXPERIMENTAL EXAMPLES but is not deemed to be limited thereto.

$^1$H-NMR spectrum was measured by Bruker AVANCE DPX-300 (300 MHz) type spectrometer using tetramethylsilane as an internal standard. All δ values are shown in ppm.

The symbols used herein have the following definitions.
s: singlet
d: doublet
dd: double doublet
t: triplet
tt: triple triplet
q: quartet
m: multiplet
br: broad
J: coupling constant
Hz: Hertz
DMF: N,N-dimethylformamide
CDCl$_3$: deuterated chloroform
DMSO-d$_6$: dimethylsulfoxide-d$_6$
IR: infrared absorption spectrum
WSC: 1-ethyl-3-(dimethylaminopropyl)carbodiimide hydrochloride
HOBt: 1-hydroxybenzotriazole The term "at room temperature" refers to the range from about 10 to 35° C., but is not to be construed as strictly limitative.

Lactose, crystalline cellulose, magnesium stearate and corn starch used in PREPARATION EXAMPLES are those that fulfill the product standards established by The Japanese Pharmacopoeia, Fourteenth Edition.

REFERENCE EXAMPLE 1

2-[(Cyclobutylcarbonyl)thio]benzoic acid

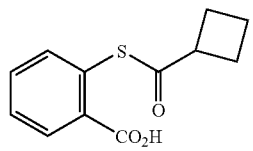

Thiosalicylic acid (6.17 g, 40 mmol) was suspended in tert-butylmethyl ether (100 ml) at room temperature. While stirring under ice cooling, pyridine (7.91 g, 100 mmol) and then cyclobutanecarbonyl chloride (5.00 g, 42 mmol) were dropwise added to the suspension. After the reaction mixture was stirred for 2 hours, the mixture was diluted with water and 6N hydrochloric acid was added thereto to make its liquid property acidic. The mixture was extracted (100 ml×3) with tert-butylmethyl ether-tetrahydrofuran (3:1, v/v). The extract was washed with saturated brine and dried over anhydrous magnesium sulfate. The solvent was removed by distillation to give the title compound (9.11 g, 96%). A part (1.0 g) of the compound was recrystallized from ethyl acetate-hexane to give colorless crystals (0.81 g).

Melting point: 92.6-95.5° C. IR (KBr): 2988, 2946, 1701, 1586, 1474, 1437, 1406, 1298, 1265, 1144, 1109, 1053, 959, 816, 748 cm$^{-1}$. $^1$H-NMR (CDCl$_3$) δ:1.83-2.58 (6H, m), 3.40-3.60 (1H, m), 7.33-7.64 (3H, m), 8.09 (1H, d, J=7.2 Hz). Elemental analysis: as C$_{12}$H$_{12}$O$_3$S Calcd.: C, 61.00; H, 5.12. Found: C, 60.88; H, 5.20.

REFERENCE EXAMPLE 2 tert-Butyl (3-cyanophenoxy)acetate

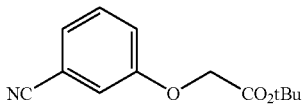

tert-Butyl bromoacetate (9.01 g, 46 mmol) was dropwise added to a mixture of 3-cyanophenol (5.0 g, 42 mmol), potassium carbonate (13.82 g, 100 mmol) and DMF (40 ml) while stirring. After stirring for 8 hours, the mixture was poured onto ice water followed by extraction with ethyl ether. The extract was washed with saturated brine. After drying over anhydrous magnesium sulfate, the solvent was concentrated under reduced pressure. The residue was applied to column chromatography using silica gel (200 g) and eluted with hexane-ethyl acetate (3:1, v/v) to give the title compound (9.70 g, 99%) as an oily substance.

IR: 2230, 1748, 1580, 1483, 1433, 1370, 1229, 1152, 1078, 845 cm$^{-1}$. $^1$H-NMR (CDCl$_3$) δ: 1.49 (9H, s), 4.54 (2H, s), 7.12 (1H, s), 7.13-7.37 (3H, m).

REFERENCE EXAMPLE 3 tert-Butyl 3-[3-(4-oxo-4H-1,3-benzothiazin-2-yl)phenyl]propionate

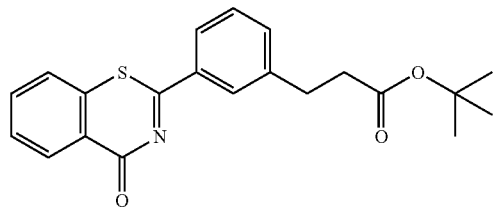

A mixture of tert-butyl 3-(3-cyanophenyl)propionate (0.74 g, 3.2 mmol), methyl thiosalicylate (1.1 g, 6.4 mmol), triethylamine (0.67 ml, 4.8 mmol) and toluene (3 ml) was heated and refluxed for 27 hours under a nitrogen flow. The reaction mixture was applied to column chromatography using silica gel (50 g). Fractions eluted with hexane-ethyl acetate (2:1, v/v) were collected and concentrated to give the title compound (0.19 g, 16%) as crystals.

$^1$H-NMR (CDCl$_3$) δ: 1.43 (9H, s), 2.61 (2H, t, J=7.5 Hz), 3.02 (2H, t, J=7.5 Hz), 7.44-7.69 (5H, m), 8.04 (1H, d, J=7.2 Hz), 8.10 (1H, s), 8.55 (1H, d, J=7.6 Hz).

REFERENCE EXAMPLE 4

2-{[4-(Acetylamino)benzoyl]thio}benzoic acid

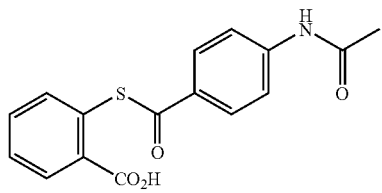

Thiosalicylic acid (1.28 g, 8.3 mmol) was suspended in tetrahydrofuran (10 ml). While stirring, pyridine (1.64 g, 21 mmol) and then a tetrahydrofuran solution (5 ml) of 4-(acetylamino)benzoyl chloride (1.67 g, 9.1 mmol) were dropwise added to the suspension under ice cooling. After the reaction mixture was stirred for 15 hours, the mixture was diluted with water and 6N hydrochloric acid was added thereto to make its liquid property acidic. The mixture was extracted (50 ml×2) with ethyl acetate. The extract was washed with saturated brine and dried over anhydrous magnesium sulfate. The solvent was removed by distillation and the residue was recrystallized from ethyl acetate-isopropyl ether to give the title compound (1.38 g, 53%).

$^1$H-NMR (DMSO-d$_6$) δ:2.65 (3H, s), 7.60-7.69 (3H, m), 7.96 (1H, d, J=8.3 Hz), 8.07-8.16 (4H, m), 13.19 (1H, br s).

REFERENCE EXAMPLE 5

2-{[2-(Methoxy)benzoyl]thio}benzoic acid

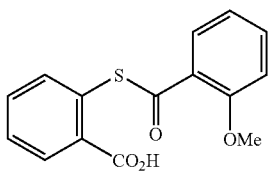

Thiosalicylic acid (1.38 g, 9.0 mmol) was suspended in tetrahydrofuran (10 ml). While stirring under ice cooling, pyridine (1.77 g, 22 mmol) and then a tetrahydrofuran solution (5 ml) of 2-methoxybenzoyl chloride (1.68 g, 9.9 mmol) were dropwise added to the suspension. After the reaction mixture was stirred for 15 hours, the mixture was diluted with water and 6N hydrochloric acid was added thereto to make its liquid property acidic. The mixture was extracted (50 ml×2) with ethyl acetate. The extract was washed with saturated brine and dried over anhydrous magnesium sulfate. The solvent was removed by distillation. The residue was recrystallized from tetrahydrofuran-isopropyl ether to give the title compound (2.08 g, 73%).

$^1$H-NMR (CDCl$_3$) δ:3.94 (3H, m), 6.98-7.03 (2H, m), 7.49-7.66 (4H, m), 7.84 (1H, d, J=8.1 Hz), 8.09 (1H, d, J=7.6 Hz).

REFERENCE EXAMPLE 6

2-[(1,1'-Biphenyl-4-ylcarbonyl)thio]benzoic acid

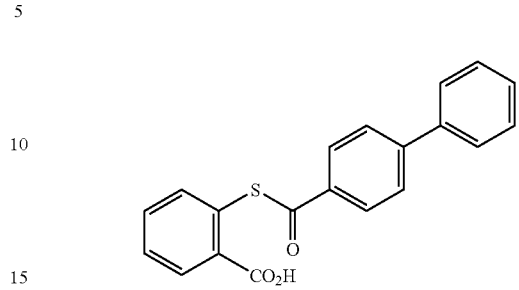

Thiosalicylic acid (1.06 g, 6.9 mmol) was suspended in tetrahydrofuran (10 ml). While stirring under ice cooling, pyridine (1.36 g, 17 mmol) and then a tetrahydrofuran solution (5 ml) of 1,1'-biphenylcarbonyl chloride (1.64 g, 7.6 mmol) were dropwise added to the suspension. After the reaction mixture was stirred for 14 hours, the mixture was diluted with water and 6N hydrochloric acid was added thereto to make its liquid property acidic. The mixture was extracted (50 ml×2) with ethyl acetate-tetrahydrofuran (3:1, v/v). The extract was washed with saturated brine and dried over anhydrous magnesium sulfate, followed by distillation to remove the solvent. The residue was recrystallized from ethyl acetate to give the title compound (1.29 g, 56%).

$^1$H-NMR (DMSO-d$_6$) δ:7.46-7.56 (3H, m), 7.60-7.68 (3H, m), 7.78 (2H, d, J=7.2 Hz), 7.91 (2H, d, J=8.5 Hz), 7.92 (1H, m), 8.06 (1H, d, J=8.5 Hz), 13.15 (1H, br s).

REFERENCE EXAMPLE 7

Methyl 2-amino-4-(aminocarbonyl)benzoate

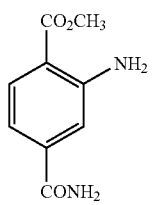

Under ice cooling, 1-hydroxy-1H-benzotriazole ammonium salt (6.86 g, 45.1 mmol) and 1-ethyl-3-(3-dimethylaminopropyl)carbodiimide hydrochloride (8.64 g, 45.1 mmol) were added to DMF solution (40 mL) of 1-methyl 2-aminoterephthalate (8.0 g, 41.0 mmol). The mixture was stirred at the same temperature for 1.5 hours and at room temperature for 30 minutes. After ice water was added to the reaction mixture, the precipitated crystals were taken by filtration and washed with water and diethyl ether. The filtrate was neutralized with sodium hydrogencarbonate, which was extracted 4 times with a tetrahydrofuran-ethyl acetate mixture. The combined organic layers were dried over sodium sulfate, filtered and concentrated under reduced pressure. The residue was crystallized from water-ethyl acetate to give the title compound (7.32 g, 92%).

$^1$H-NMR (DMSO-d$_6$) δ: 3.80 (3H, s), 6.74 (2H, s), 6.94 (1H, dd, J=8.4, 1.8 Hz), 7.24 (1H, d, J=1.8 Hz), 7.37 (1H, br s), 7.72 (1H, d, J=8.4 Hz), 7.91 (1H, br s).

REFERENCE EXAMPLE 8

Methyl 4-cyano-2-[(trifluoroacetyl)amino]benzoate

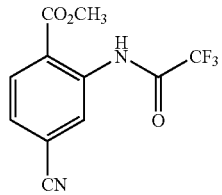

Under ice cooling, triethylamine (6.43 mL, 45.5 mmol) and trifluoroacetic anhydride (6.34 mL, 45.5 mmol) were added to a tetrahydrofuran solution (40 mL) of methyl 2-amino-4-(aminocarbonyl)benzoate (4.02 g, 20.7 mmol). The mixture was stirred at the same temperature for 30 minutes. After ice water was added to the reaction mixture, the mixture was extracted twice with ethyl acetate. The combined organic layers were washed with saturated sodium chloride aqueous solution and dried over magnesium sulfate, filtered and concentrated under reduced pressure. The residue was applied to silica gel column chromatography (hexane/ethyl acetate=10:1) to give the title compound (5.65 g, quantitative).

$^1$H-NMR (CDCl$_3$) δ: 4.03 (3H, s), 7.53 (1H, dd, J=8.2, 1.4 Hz), 8.22 (1H, d, J=8.2 Hz), 9.04 (1H, d, J=1.4 Hz), 12.30 (1H, br s).

REFERENCE EXAMPLE 9

Methyl 2-amino-4-cyanobenzoate

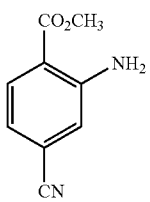

Potassium carbonate (60.3 g, 436 mmol) was added to a methanol suspension (850 mL) of methyl 4-cyano-2-[(trifluoroacetyl)amino]benzoate (108 g, 397 mmol) and the mixture was stirred at 50° C. for 2 hours. After cooling, methanol was distilled off under reduced pressure and water was added to the residue. The mixture was extracted twice with ethyl acetate. The combined organic layers were washed with 0.5M hydrochloric acid and then saturated brine, dried over sodium sulfate, filtered and concentrated under reduced pressure. The residue was crystallized from ethyl acetate-diisopropyl ether to give the title compound (53.9 g, 76%).

$^1$H-NMR (CDCl$_3$) δ: 3.90 (3H, s), 5.93 (2H, br s), 6.87 (1H, dd, J=8.4, 1.8 Hz), 6.94 (1H, d, J=1.8 Hz), 7.93 (1H, d, J=8.4 Hz).

REFERENCE EXAMPLE 10

Methyl 4-cyano-2-(ethylamino)benzoate

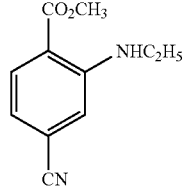

Acetaldehyde (90%)(10 mL) and sodium triacetoxyborohydride (7.71 g, 36.4 mmol) were added to an acetic acid solution (10 mL) of methyl 2-amino-4-cyanobenzoate (3.04 g, 17.3 mmol) under ice cooling. The mixture was stirred at the same temperature for an hour and at room temperature for 2 hours. Ice water was added to the reaction mixture, the mixture was neutralized with sodium hydrogencarbonate, followed by extraction with ethyl acetate. The combined organic layers were washed with water and then saturated brine, dried over sodium sulfate, filtered and concentrated under reduced pressure. The crystals obtained were washed with diisopropyl ether-hexane to give the title compound (800 mg, 23%). The residue was applied to silica gel column chromatography (hexane/ethyl acetate=50:1 and then 30:1). The crystals obtained were washed with hexane to give the title compound (920 mg, 26%).

$^1$H-NMR (CDCl$_3$) δ: 1.34 (3H, t, J=7.0 Hz), 3.16-3.29 (2H, m), 3.88 (3H, s), 6.77-6.82 (1H, m), 6.90 (1H, s), 7.77 (1H, br s), 7.95 (1H, d, J=7.6 Hz).

REFERENCE EXAMPLE 11

3-[(5-Oxo-2-phenyl-1,3-oxazol-4(5H)-ylidene)methyl]benzonitrile

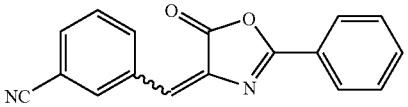

An acetic anhydride suspension (10 mL) of 3-cyanobenzaldehyde (1.32 g, 10.1 mmol), hippuric acid (1.81 g, 10.1 mmol) and sodium acetate (826 mg, 10.1 mmol) was stirred at 100° C. for 30 minutes. After the reaction mixture was allowed to cool and diethyl ether was added thereto, the solid was taken out by filtration and the filtrate was concentrated under reduced pressure. The solid obtained and the residue were combined and the mixture was suspended in a mixture of ethyl acetate-water. After filtering, the solid was dissolved in dichloromethane, followed by washing with water. The mixture was dried over sodium sulfate, filtered and concentrated under reduced pressure to give the title compound (2.04 g, 74%).

$^1$H-NMR (CDCl$_3$) δ: 7.17 (1H, s), 7.53-7.73 (5H, m), 8.18-8.28 (3H, m), 8.67 (1H, t, J=1.7 Hz).

REFERENCE EXAMPLE 12

Methyl 2-(benzoylamino)-3-(3-cyanophenyl)-2-propenoate

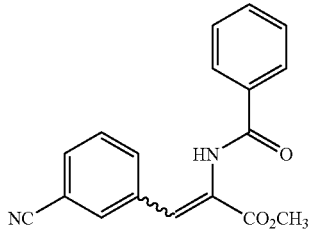

A suspension of 3-[(5-oxo-2-phenyl-1,3-oxazol-4(5H)-ylidene)-methyl]benzonitrile (1.98 g, 9.01 mmol) and sodium carbonate (26 mg, 0.25 mmol) in methanol was heated under reflux for 2.5 hours. After the reaction mixture was concentrated under reduced pressure, ethyl acetate and water were added to the residue to separate the organic layer. The aqueous layer was extracted with ethyl acetate. The combined organic layers were washed with water and concentrated under reduced pressure. The residue was applied to silica gel column chromatography (gradient elution with hexane-ethyl acetate from 80:20 to 33:67) and recrystallized from acetone-diisopropyl ether to give the title compound (1.63 g, 74%).

$^1$H-NMR (CDCl$_3$) δ: 3.91 (3H, s), 7.39-7.61 (6H, m), 7.63-7.68 (1H, m), 7.70-7.72 (1H, m), 7.81-7.86 (2H, m), 8.02 (1H, br s).

REFERENCE EXAMPLE 13

Methyl 2-(benzoylamino)-3-(3-cyanophenyl)propionate

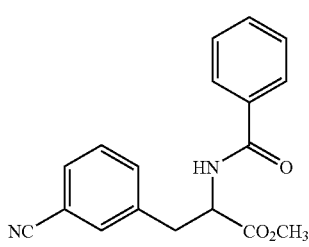

A suspension of methyl 2-(benzoylamino)-3-(3-cyanophenyl)2-propenoate (300 mg, 0.979 mmol) and 5% palladium/barium sulfate (60 mg) in tetrahydrofuran (3 mL) was stirred at 50° C. for 7.5 hours under a hydrogen flow. The catalyst was filtered off and the filtrate was concentrated under reduced pressure. The residue was dissolved in tetrahydrofuran (3 mL) and 5% palladium/barium sulfate (90 mg) was added to the solution. The mixture was stirred at 50° C. for 8 hours under a hydrogen flow. The catalyst was filtered off and the filtrate was concentrated under reduced pressure. The residue was crystallized from ethyl acetate-hexane to give the title compound (273 mg, 90%).

$^1$H-NMR (CDCl$_3$) δ: 3.24 (1H, dd, J=14.0, 5.6 Hz), 3.37 (1H, dd, J=14.0, 5.6 Hz), 3.79 (3H, s), 5.09 (1H, dt, J=6.8, 5.6 Hz), 6.63 (1H, br d, J=6.8 Hz), 7.38-7.48 (5H, m), 7.50-7.57 (2H, m), 7.70-7.76 (2H, m).

EXAMPLES

Example 1

2-Cyclopropyl-4H-1,3-benzothiazin-4-one

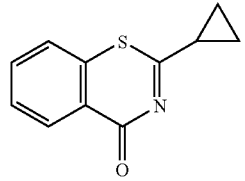

2-[(Cyclopropylcarbonyl)thio]benzoic acid (11.11 g, 50 mmol) was suspended in acetone (150 ml). While stirring under ice cooling, triethylamine (5.10 g, 50 mmol) and then ethyl chloroformate (6.68 g, 62 mmol) were dropwise added to the suspension. After stirring at the same temperature for an hour, an aqueous solution (15 ml) of sodium azide (5.00 g, 77 mmol) was dropwise added to the reaction mixture and stirring was continued for further an hour. The reaction mixture was diluted with water and the dilution was extracted with toluene (100 ml×3). The extract was washed with saturated brine, dried over anhydrous magnesium sulfate and then filtered. The toluene solution was cooled to about −15° C. and a solution (10 ml) of tributylphosphine (10.50 g, 52 mmol) in toluene was dropwise added to the solution. After completion of the dropwise addition, the reaction temperature was reverted to room temperature and the mixture was heated under reflux for 15 minutes. The reaction solution was concentrated under reduced pressure. The residue was applied to column chromatography using silica gel (300 g) to elute with hexane-ethyl acetate (2:1, v/v). The eluate was recrystallized from ethyl acetate-hexane to give the title compound (2.85 g, 28%) as crystals.

Melting point: 119.5-119.6° C. IR (KBr): 1651, 1574, 1537, 1433, 1381, 1296, 1235, 1204, 1136, 1094, 1069, 1013, 866, 745 cm$^{-1}$. $^1$H-NMR (CDCl$_3$) δ:1.09-1.33 (2H, m), 1.15-1.76 (2H, m), 1.95-2.16 (1H, m), 7.34-7.71 (3H, m), 8.36-8.56 (1H, m). Elemental analysis: as C$_{11}$H$_9$NOS Calcd.: C, 65.00; H, 4.46; N, 6.89. Found: C, 65.13; H, 4.52; N, 7.00.

Example 2

2-Cyclobutylidene-2,3-dihydro-4H-1,3-benzothiazin-4-one

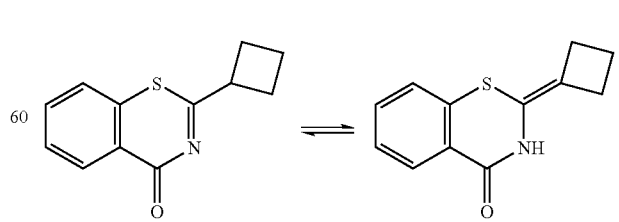

2-[(Cyclobutylcarbonyl)thio]benzoic acid (9.01 g, 38 mmol) was suspended in acetone (150 ml). While stirring under ice cooling, triethylamine (4.25 g, 42 mmol) and then ethyl chloroformate (4.88 g, 45 mmol) were dropwise added to the suspension. After stirring at the same temperature for an hour, an aqueous solution (15 ml) of sodium azide (2.92 g, 45 mmol) was dropwise added to the reaction mixture, followed by further stirring for an hour. The reaction mixture was diluted with water and the dilution was extracted with toluene. The extract was washed with saturated brine, dried over anhydrous magnesium sulfate and then filtered. The toluene solution was cooled to about −15° C. and a solution (15 ml) of tributylphosphine (7.70 g, 38 mmol) in toluene was dropwise added to the solution. After completion of the dropwise addition, the reaction temperature was reverted to room temperature and the mixture was heated under reflux for 10 minutes. The reaction solution was concentrated under reduced pressure. The residue was recrystallized from toluene-isopropyl ether to give the title compound (3.32 g, 40%) as crystals.

Melting point: 146.7-149.4° C. IR (KBr): 3169, 1671, 1588, 1466, 1443, 1383, 1275, 1246, 1231, 1190, 1159, 1107, 1064, 1034, 976, 955, 814 cm$^{-1}$. $^1$H-NMR (CDCl$_3$) δ:1.85-209 (2H, m), 2.43-2.85 (4H, m), 7.13-7.56 (3H, m), 7.94 (1H, d, J=7.8 Hz), 10.13 (1H, br s). Elemental analysis: as C$_{12}$H$_{11}$NOS Calcd.: C, 66.33; H, 5.10; N, 6.45. Found: C, 66.23; H, 5.21; N, 6.51.

Example 3

2-Cyclopentylidene-2,3-dihydro-4H-1,3-benzothiazin-4-one

2-[(Cyclopentylcarbonyl)thio]benzoic acid (11.53 g, 46 mmol) was suspended in acetone (150 ml). While stirring under ice cooling, triethylamine (5.10 g, 50 mmol) and then ethyl chloroformate (6.68 g, 62 mmol) were dropwise added to the suspension. After stirring at the same temperature for an hour, an aqueous solution (15 ml) of sodium azide (5.00 g, 77 mmol) was dropwise added to the reaction mixture, followed by further stirring for an hour. The reaction mixture was diluted with water and the dilution was extracted with toluene (100 ml×3). The extract was washed with saturated brine, dried over anhydrous magnesium sulfate and then filtered. The toluene solution was cooled to about −15° C. and a solution (10 ml) of tributylphosphine (10.50 g, 52 mmol) in toluene was dropwise added to the solution. After completion of the dropwise addition, the reaction temperature was reverted to room temperature and the mixture was heated under reflux for 15 minutes. The reaction solution was concentrated under reduced pressure. The residue was recrystallized from acetone-ethyl acetate to give the title compound (2.02 g, 19%) as crystals.

Melting point: 190.4-191.4° C. IR (KBr):3163, 3040, 2870, 1647, 1590, 1447, 1379, 1244, 1177, 1065, 1030, 893, 775 cm$^{-1}$. $^1$H-NMR (CDCl$_3$) δ:1.53-1.76 (4H, m), 2.18 (2H, br s), 2.34 (2H, br s), 7.18-7.52 (3H, m), 7.94 (1H, d, J=7.7 Hz), 9.90 (1H, br s). Elemental analysis: as C$_{13}$H$_{13}$NOS Calcd.: C, 67.50; H, 5.66; N, 6.06. Found: C, 67.46; H, 5.73; N, 6.13.

Example 4

2-Cyclohexylidene-2,3-dihydro-4H-1,3-benzothiazin-4-one

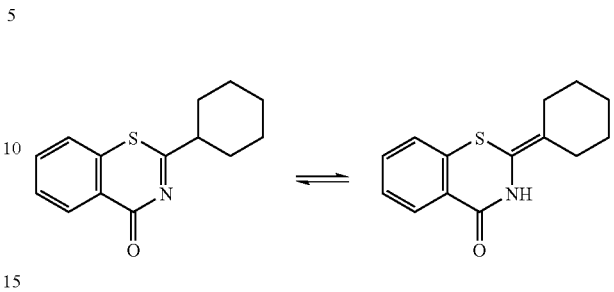

2-[(Cyclohexylcarbonyl)thio]benzoic acid (14.77 g, 56 mmol) was suspended in acetone (150 ml). While stirring under ice cooling, triethylamine (5.10 g, 50 mmol) and then ethyl chloroformate (6.70 g, 62 mmol) were dropwise added to the suspension. After stirring at the same temperature for 40 minutes, an aqueous solution (20 ml) of sodium azide (5.00 g, 77 mmol) was dropwise added to the reaction mixture, followed by further stirring for an hour. The reaction mixture was diluted with water and the dilution was extracted with toluene (100 ml×3). The extract was washed with saturated brine, dried over anhydrous magnesium sulfate and then filtered. The toluene solution was cooled to about −15° C. and a solution (10 ml) of tributylphosphine (10.37 g, 51 mmol) in toluene was dropwise added to the solution. After completion of the dropwise addition, the reaction temperature was reverted to room temperature and the mixture was heated under reflux for 15 minutes. The reaction solution was concentrated under reduced pressure. The residue was applied to column chromatography using silica gel (150 g) to elute with hexane-ethyl acetate (2:1, v/v). The eluate was crystallized from acetone-ethyl acetate to give the title compound (1.16 g, 10%) as crystals.

Melting point: 145.6-147.1° C. IR (KBr):1655 cm$^{-1}$. $^1$H-NMR (CDCl$_3$) δ:1.19-2.07 (8H, m), 1.72-2.43 (3H, m), 7.13-7.30 (2H, m), 7.38 (1H, t, J=6.2 Hz), 8.09 (1H, d, J=7.4 Hz). Elemental analysis: as C$_{14}$H$_{15}$NOS Calcd.: C, 68.54; H, 6.16; N, 5.71. Found: C, 68.59; H, 5.94; N, 5.77.

Example 5

2-Isopropylidene-2,3-dihydro-4H-1,3-benzothiazin-4-one

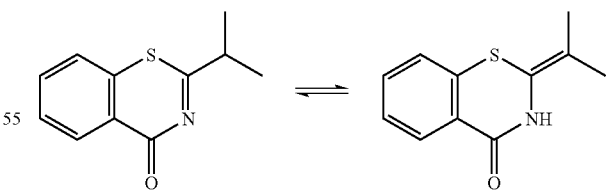

2-[(Isopropylcarbonyl)thio]benzoic acid (11.20 g, 50 mmol) was suspended in acetone (150 ml). While stirring under ice cooling, triethylamine (5.10 g, 50 mmol) and then ethyl chloroformate (6.68 g, 62 mmol) were dropwise added to the suspension. After stirring at the same temperature for an hour, an aqueous solution (15 ml) of sodium azide (5.00 g, 77 mmol) was dropwise added to the reaction mixture, followed by further stirring for an hour. The reaction mixture was diluted with water and the dilution was extracted with toluene (100 ml×3). The extract was washed with saturated brine, dried over anhydrous magnesium sulfate and then filtered. The toluene solution was cooled to about −15° C. and a solution (10 ml) of tributylphosphine (10.50 g, 52 mmol) in toluene was dropwise added to the solution. After completion of the dropwise addition, the reaction temperature was reverted to room temperature and the mixture was heated under reflux for 15 minutes. The reaction solution was concentrated under reduced pressure. The residue was recrystallized from ethanol-ethyl acetate to give the title compound (3.03 g, 30%) as crystals.

Melting point: 187.1-188.3° C. IR (KBr):3169, 3042, 1644, 1588, 1445, 1387, 1366, 1258, 1194, 1067, 910, 777 cm$^{-1}$. $^1$H-NMR (CDCl$_3$) δ:1.81 (3H, s), 1.84 (3H, s), 7.08-7.25 (2H, m), 7.39 (1H, dt, J=1.5, 7.6 Hz), 8.09 (1H, br s), 8.11 (1H, dd, J=1.5, 7.8 Hz). Elemental analysis: as C$_{11}$H$_{11}$NOS Calcd.: C, 64.36; H, 5.40; N, 6.82. Found: C, 64.35; H, 5.29; N, 6.65.

Example 6 tert-Butyl (3-(4-oxo-4H-1,3-benzothiazin-2-yl)phenoxy)acetate

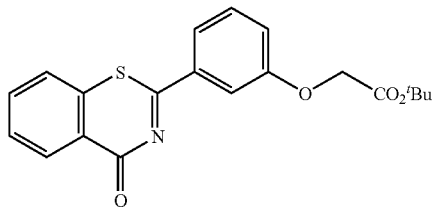

A mixture of tert-butyl (3-cyanophenoxy)acetate (4.64 g, 20 mmol), methyl thiosalicylate (3.70 g, 24 mmol), triethylamine (2.54 g, 25 mmol) and toluene (15 ml) was heated and refluxed for 20 hours under a nitrogen flow. After the solvent was distilled off under reduced pressure, the residue was applied to column chromatography using silica gel. From the fractions eluted with hexane-ethyl acetate (3:1, v/v), the title compound (1.46 g, 20%) was obtained as crystals.

IR: 1750, 1655, 1570, 1522, 1437, 1368, 1289, 1231, 1155, 1098, 1030, 912 cm$^{-1}$. $^1$H-NMR (CDCl$_3$) δ: 1.51 (9H, s), 4.63 (2H, s), 7.13-7.23 (1H, m), 7.44 (1H, t, J=8.1 Hz), 7.50-7.83 (5H, m), 8.49-8.55 (1H, m).

Example 7

3-[3-(4-Oxo-4H-1,3-benzothiazin-2-yl)phenyl]propionic acid

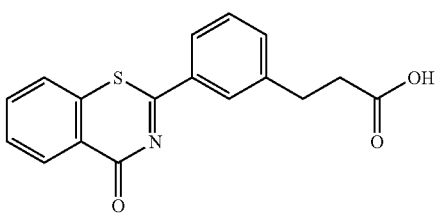

After tert-butyl 3-[3-(4-oxo-4H-1,3-benzothiazin-2-yl)phenyl]propionate (0.19 g, 0.52 mmol) was dissolved in trifluoroacetic acid (1.0 ml), the mixture was stirred at room temperature for 2 hours. Isopropyl ether was added to the reaction solution and the precipitated crystals were taken by filtration. The precipitates were recrystallized from ethanol-isopropyl ether to give the title compound (0.056 g, 35%) as crystals.

Melting point: 179.8-180.2° C. $^1$H-NMR (DMSO-d$_6$) δ: 2.63 (2H, t, J=7.4 Hz), 2.97 (2H, t, J=7.4 Hz), 7.53-7.63 (2H, m), 7.74-7.87 (3H, m), 7.99 (1H, d, J=7.7 Hz), 8.02 (1H, s), 8.36 (1H, d, J=8.1 Hz), 12.16 (1H, s). IR: 3229, 1732, 1630, 1512, 1439 cm$^{-1}$. Elemental analysis: as C$_{17}$H$_{13}$NO$_3$S.0.5H$_2$O Calcd.: C, 63.73; H, 4.40; N, 4.37. Found: C, 63.72; H, 4.16; N, 4.42.

Example 8

2-(3-Cyanophenyl)-4H-1,3-benzothiazin-4-one

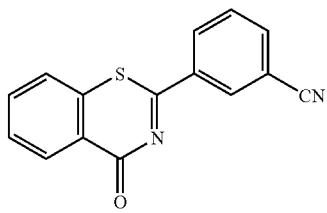

A mixture of isophthalonitrile (1.00 g, 07.8 mmol), methyl thiosalicylate (1.97 g, 12 mmol), triethylamine (1.34 g, 13 mmol) and toluene (5 ml) was heated and refluxed for 5 hours under a nitrogen flow. The precipitated crystals were taken by filtration and recrystallized from tetrahydrofuran-ethanol to give the title compound (0.07 g, 2%) as crystals.

Melting point: 199.6-199.7° C. IR: 2230, 1667, 1587, 1570, 1520, 1477, 1440, 1294, 1149, 1097, 1028, 912 cm$^{-1}$. $^1$H-NMR (CDCl$_3$) δ: 7.58-7.74 (4H, m), 7.90 (1H, d, J=7.8 Hz), 8.45 (1H, d, J=8.0 Hz), 8.51 (1H, s), 8.57 (1H, d, J=7.6 Hz). Elemental analysis: as C$_{15}$H$_8$N$_2$OS.0.25H$_2$O Calcd.: C, 67.02; H, 3.19; N, 10.42. Found: C, 67.32; H, 3.22; N, 10.40.

Example 9

2-(4-Trifluoromethylphenyl)-4H-1,3-benzothiazin-4-one

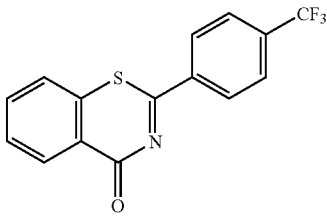

A mixture of 4-trifluoromethylbenzonitrile (2.00 g, 12 mmol), methyl thiosalicylate (3.93 g, 23 mmol), triethylamine (2.40 g, 24 mmol) and toluene (10 ml) was heated and refluxed for 25 hours under a nitrogen flow. The reaction solution was concentrated under reduced pressure and the residue was applied to column chromatography using silica gel (100 g). Fractions eluted with hexane-ethyl acetate (5:1, v/v) were concentrated under reduced pressure. The residue was recrystallized from isopropyl ether to give the title compound (0.58 g, 16%) as crystals.

Melting point: 122.5-122.6° C. IR: 1651, 1587, 1570, 1522, 1458, 1439, 1408, 1332, 1316, 1159, 1113, 1068, 1013, 930 cm$^{-1}$. $^1$H-NMR (CDCl$_3$) δ: 7.57-7.73 (3H, m), 7.81 (2H, d, J=8.3 Hz), 8.33 (2H, d, J=8.3 Hz), 8.57 (1H, d, J=7.5 Hz). Elemental analysis: as C$_{15}$H$_8$NOSF$_3$ Calcd.: C, 58.63; H, 2.62; N, 4.56 Found: C, 58.42; H, 2.70; N, 4.48

Example 10

2-(4-Acetylphenyl)-4H-1,3-benzothiazin-4-one

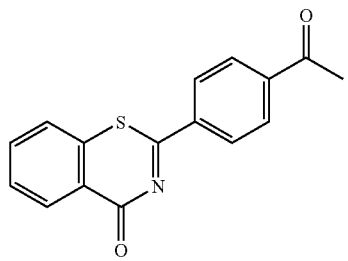

A mixture of 4-acetylbenzonitrile (2.00 g, 14 mmol), methyl thiosalicylate (4.63 g, 28 mmol), triethylamine (2.79 g, 28 mmol) and toluene (10 ml) was heated and refluxed for 72 hours under a nitrogen flow. The reaction solution was concentrated under reduced pressure and the residue was applied to column chromatography using silica gel (100 g). Fractions eluted with hexane-ethyl acetate (3:1, v/v) were concentrated under reduced pressure. The residue was recrystallized from isopropyl ether to give the title compound (0.07 g, 2%) as crystals.

Melting point: 197.5-197.6° C. IR: 1678, 1661, 1587, 1578, 1524, 1440, 1404, 1358, 1287, 1275, 1242, 1098, 927 cm$^{-1}$. $^1$H-NMR (CDCl$_3$) δ: 2.68 (3H, s), 7.57-7.72 (3H, m), 8.10 (2H, d, J=8.6 Hz), 8.32 (2H, d, J=8.6 Hz), 8.57 (1H, d, J=7.5 Hz). Elemental analysis: as C$_{16}$H$_{11}$NO$_2$S.0.2H$_2$O Calcd.: C, 67.44; H, 4.03; N, 4.92. Found: C, 67.73; H, 3.79; N, 4.86.

Example 11

2-(3-Bromophenyl)-4H-1,3-benzothiazin-4-one

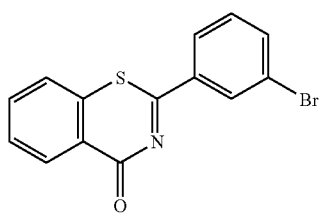

A mixture of 3-bromobenzonitrile (2.00 g, 11 mmol), methyl thiosalicylate (2.87 g, 17 mmol), triethylamine (1.95 g, 19 mmol) and toluene (10 ml) was heated and refluxed under a nitrogen flow for 40 hours. The precipitated crystals were taken by filtration and recrystallized from tetrahydrofuran-ethyl acetate to give the title compound (0.72 g, 21%) as crystals.

Melting point: 161.6-161.7° C. IR: 1655, 1591, 1572, 1518, 1464, 1442, 1420, 1294, 1217, 1101, 1074, 1026 cm$^{-1}$. $^1$H-NMR (CDCl$_3$) δ: 7.41 (1H, t, J=8.0 Hz), 7.57-7.75 (4H, m), 8.13 (1H, d, J=7.8 Hz), 8.39 (1H, s), 8.57 (1H, d, J=7.6 Hz). Elemental analysis: as C$_{14}$H$_8$NOSBr Calcd.: C, 52.85; H, 2.53; N, 4.40. Found: C, 52.76; H, 2.52; N, 4.33.

Example 12

2-(4-Hydroxyphenyl)-4H-1,3-benzothiazin-4-one

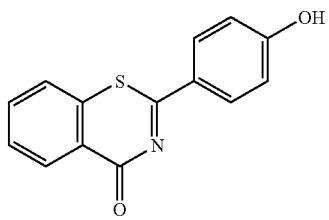

A mixture of 4-acetoxybenzonitrile (1.35 g, 8.4 mmol), methyl thiosalicylate (2.12 g, 13 mmol), triethylamine (1.50 g, 15 mmol) and toluene (10 ml) was heated and refluxed under a nitrogen flow for 26 hours. The precipitated crystals were taken by filtration and recrystallized from tetrahydrofuran-ethyl acetate to give the title compound (0.34 g, 16%) as crystals.

Melting point: 275° C. (decomposed) IR: 3150, 1626, 1604, 1587, 1570, 1493, 1458, 1327, 1289, 1252, 1240, 1178, 1103 cm$^{-1}$. $^1$H-NMR (DMSO-d$_6$) δ: 6.98 (2H, d, J=8.8 Hz), 7.67-7.84 (3H, m), 8.07 (2H, d, J=8.8 Hz), 8.32 (1H, d, J=7.7 Hz). Elemental analysis: as C$_{14}$H$_9$NO$_2$S.0.2H$_2$O Calcd.: C, 64.95; H, 3.66; N, 5.41. Found: C, 65.26; H, 3.78; N, 5.38.

Example 13

N-[3-(4-Oxo-4H-1,3-benzothiazin-2-yl)phenyl]acetamide

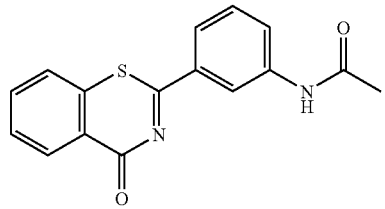

A mixture of N-(3-cyanophenyl)acetamide (2.00 g, 13 mmol), methyl thiosalicylate (3.20 g, 19 mmol), triethylamine (2.30 g, 23 mmol) and toluene (15 ml) was heated and refluxed for 25 hours under a nitrogen flow. The solvent was concentrated under reduced pressure. After washing with isopropyl ether and ethanol, the residue was recrystallized from tetrahydrofuran-ethyl acetate to give the title compound (0.07 g, 2%) as crystals.

Melting point: 241.4-241.5° C. IR: 3256, 1686, 1642, 1591, 1570, 1518, 1485, 1443, 1406, 1367, 1298, 1250, 1192, 1103, 993 cm$^{-1}$. $^1$H-NMR (DMSO-d$_6$) δ: 2.10 (3H, s), 7.56 (1H, t, J=8.0 Hz), 7.72-7.92 (5H, m), 8.36 (1H, d, J=7.6 Hz), 8.51 (1H, s), 10.29 (1H, s).

Example 14

2-(4-Cyanophenyl)-4H-1,3-benzothiazin-4-one

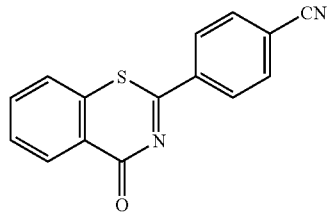

A mixture of terephthalonitrile (1.50 g, 12 mmol), methyl thiosalicylate (2.95 g, 18 mmol), triethylamine (2.10 g, 21 mmol) and toluene (20 ml) was heated and refluxed under a nitrogen flow for 48 hours. The crystals precipitated were taken by filtration and recrystallized from tetrahydrofuran to give the title compound (0.98 g, 32%) as crystals.

Melting point: 241.3-241.4° C. IR: 2230, 1659, 1587, 1574, 1520, 1440, 1402, 1298, 1281, 1238, 1128, 1094, 924 cm$^{-1}$. $^1$H-NMR (CDCl$_3$) δ: 7.57-7.74 (3H, m), 7.84 (2H, d, J=8.6 Hz), 8.32 (2H, d, J=8.6 Hz), 8.57 (1H, d, J=7.5 Hz).

Example 15

N,N-Diethyl-4-(4-oxo-4H-1,3-benzothiazin-2-yl)benzamide

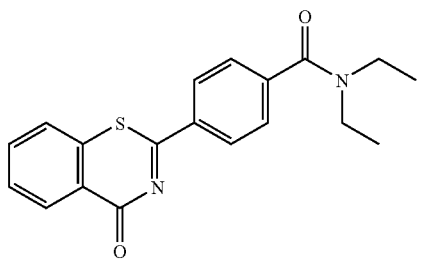

A mixture of 4-cyano-N,N-diethylbenzamide (0.60 g, 3.0 mmol), methyl thiosalicylate (0.75 g, 4.5 mmol), triethylamine (0.54 g, 5.3 mmol) and toluene (5 ml) was heated and refluxed under a nitrogen flow for 70 hours. To the reaction solution, ethyl acetate was added and the solid precipitated was removed by filtration. After the filtrate was ice-cooled, the crystals precipitated were taken by filtration and recrystallized from ethyl acetate to give the title compound (0.31 g, 30%) as crystals.

Melting point: 180.0-180.1° C. IR: 1662, 1628, 1572, 1522, 1458, 1439, 1310, 1287, 1236, 1095, 926 cm$^{-1}$. $^1$H-NMR (CDCl$_3$) δ: 1.13 (3H, m), 1.26 (3H, m), 3.25 (2H, m), 3.58 (2H, m), 7.54 (2H, d, J=8.5 Hz), 7.55-7.71 (3H, m), 8.25 (2H, d, J=8.5 Hz), 8.56 (1H, d, J=7.5 Hz).

Example 16

N-[4-(4-Oxo-4H-1,3-benzothiazin-2-yl)phenyl]acetamide

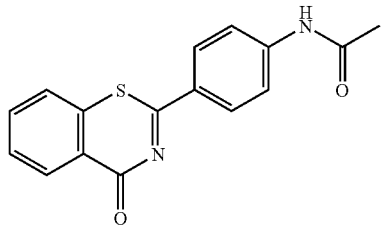

2-{[4-(Acetylamino)benzoyl]thio}benzoic acid (1.10 g, 3.5 mmol) was suspended in acetone (10 ml). While stirring under ice cooling, triethylamine (0.50 g, 4.9 mmol) and then ethyl chloroformate (0.53 g, 3.8 mmol) were dropwise added to the suspension. After stirring at the same temperature for an hour, an aqueous solution (10 ml) of sodium azide (0.34 g, 5.2 mmol) was dropwise added to the reaction mixture, followed by further stirring for an hour. The reaction mixture was diluted with water and the dilution was extracted with toluene (100 ml×2). The extract was washed with saturated brine, dried over anhydrous magnesium sulfate and then filtered. The toluene solution was cooled to about −10° C. and tributylphosphine (0.85 g, 4.2 mmol) was dropwise added to the solution. After completion of the dropwise addition, the reaction temperature was reverted to room temperature and the mixture was heated under reflux for 15 minutes. The reaction solution was concentrated under reduced pressure and washed with isopropyl ether. Then, the residue was recrystallized from tetrahydrofuran-ethanol to give the title compound (0.30 g, 29%) as crystals.

Melting point: 231.4-231.5° C. IR (KBr): 3438, 1678, 1667, 1587, 1578, 1523, 1440, 1404, 1360, 1286, 1242, 1095, 1030, 927 cm$^{-1}$. $^1$H-NMR (DMSO-d$_6$) δ:2.67 (3H, s), 7.74-7.93 (3H, m), 8.17 (2H, d, J=8.5 Hz), 8.28 (2H, d, J=8.5 Hz), 8.38 (1H, d, J=7.6 Hz). Elemental analysis: as C$_{16}$H$_{12}$N$_2$O$_2$S Calcd.: C, 64.85; H, 4.08; N, 9.45. Found: C, 64.57; H, 4.13; N, 9.75.

Example 17

2-(2-Methoxyphenyl)-4H-1,3-benzothiazin-4-one

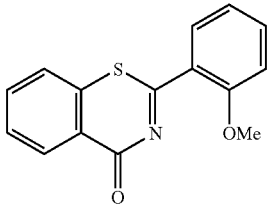

2-{[2-(Methoxy)benzoyl]thio}benzoic acid (1.90 g, 3.5 mmol) was suspended in acetone (10 ml). While stirring under ice cooling, triethylamine (0.93 g, 9.2 mmol) and then ethyl chloroformate (0.99 g, 7.3 mmol) were dropwise added to the suspension. After stirring at the same temperature for an hour, an aqueous solution (10 ml) of sodium azide (0.64 g, 9.9 mmol) was dropwise added to the reaction mixture, followed by further stirring for an hour. The reaction mixture was diluted with water and the dilution was extracted with toluene (100 ml×2). The extract was washed with saturated brine, dried over anhydrous magnesium sulfate and then filtered. The toluene solution was cooled to about −10° C. and tributylphosphine (1.60 g, 7.9 mmol) was dropwise added to the solution. After completion of the dropwise addition, the reaction temperature was reverted to room temperature and the mixture was heated under reflux for 15 minutes. The reaction solution was concentrated under reduced pressure and recrystallized from ethanol to give the title compound (0.99 g, 56%) as crystals.

Melting point: 144.2-144.3° C. IR (KBr): 1639, 1591, 1582, 1497, 1458, 1443, 1318, 1294, 1251, 1120, 1018, 928 cm$^{-1}$. $^1$H-NMR (CDCl$_3$) δ:4.00 (3H, s), 7.04 (1H, d, J=8.3 Hz), 7.09 (1H, t, J=7.9 Hz), 7.51-7.66 (4H, m), 8.15 (1H, d, J=7.9 Hz), 8.54 (1H, d, J=7.5 Hz).

Example 18

2-(1,1'-Biphenyl-4-yl)-4H-1,3-benzothiazin-4-one

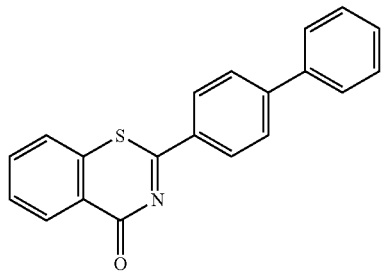

2-[(1,1'-Biphenyl-4-ylcarbonyl)thio]benzoic acid (1.15 g, 3.4 mmol) was suspended in acetone (10 ml). While stirring under ice cooling, triethylamine (0.49 g, 4.8 mmol) and then ethyl chloroformate (0.52 g, 3.8 mmol) were dropwise added to the suspension. After stirring at the same temperature for an hour, an aqueous solution (10 ml) of sodium azide (0.34 g, 5.2 mmol) was dropwise added to the reaction mixture, followed by further stirring for an hour. The reaction mixture was diluted with water and the dilution was extracted with toluene (100 ml×2). The extract was washed with saturated brine, dried over anhydrous magnesium sulfate and then filtered. The toluene solution was cooled to about −10° C. and tributylphosphine (0.84 g, 4.2 mmol) was dropwise added to the solution. After completion of the dropwise addition, the reaction temperature was reverted to room temperature and the mixture was heated under reflux for 15 minutes. The reaction solution was concentrated under reduced pressure and recrystallized from ethyl acetate-ethanol to give the title compound (0.67 g, 61%) as crystals.

Melting point: 170.5-170.9° C. IR (KBr): 1655, 1599, 1570, 1510, 1485, 1439, 1404, 1315, 1298, 1246, 1098, 928 cm$^{-1}$. $^1$H-NMR (CDCl$_3$) δ:7.44-7.69 (8H, m), 7.76 (2H, d, J=8.5 Hz), 8.31 (2H, d, J=8.5 Hz), 8.56 (1H, d, J=7.5 Hz).

Example 19

2-(2-Trifluoromethylphenyl)-4H-1,3-benzothiazin-4-one

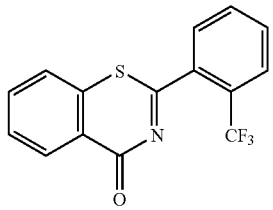

Thiosalicylic acid (4.62 g, 30 mmol) was suspended in diethyl ether (40 ml). While stirring under ice cooling, pyridine (6.00 g, 76 mmol) and then 2-trifluorobenzoyl chloride (7.30 g, 35 mmol) were dropwise added to the suspension. After the reaction mixture was stirred for an hour at the same temperature, the mixture was diluted with water and 6N hydrochloric acid was added thereto to make its liquid property acidic. The mixture was extracted (100 ml×2) with diethyl ether-ethyl acetate (1:2, v/v). The extract was washed with saturated brine and dried over anhydrous magnesium sulfate. The solvent was removed by distillation to give 2-[(2-trifluoromethylphenyl)carbonyl]thiobenzoic acid.

2-[(2-Trifluoromethylphenyl)carbonyl]thiobenzoic acid obtained above was suspended in acetone (90 ml). While stirring under ice cooling, triethylamine (2.53 g, 25 mmol) and then isobutyl chloroformate (4.10 g, 30 mmol) were dropwise added to the suspension. After stirring at the same temperature for 40 minutes, an aqueous solution (10 ml) of sodium azide (2.31 g, 36 mmol) was dropwise added to the reaction mixture, followed by further stirring for an hour. The reaction mixture was diluted with water and the dilution was extracted with toluene (30 ml×3). The extract was washed with saturated brine, dried over anhydrous magnesium sulfate and then filtered. The toluene solution was cooled to about −10° C. and a solution (10 ml) of tributylphosphine (6.07 g, 30 mmol) in toluene was dropwise added to the solution. After completion of the dropwise addition, the reaction temperature was reverted to room temperature and the mixture was heated under reflux for 10 minutes. The reaction solution was concentrated under reduced pressure and crystallized from toluene. The crystals were recrystallized from ethyl acetate-isopropyl ether to give the title compound (3.47 g, 38%) as crystals.

Melting point: 139.6-139.8° C. Elemental analysis: as C$_{15}$H$_8$NOSF$_3$ Calcd.: C, 58.63; H, 2.62; N, 4.56 Found: C, 58.80; H, 2.84; N, 4.58

Example 20

2-(3-Trifluoromethylphenyl)-4H-1,3-benzothiazin-4-one

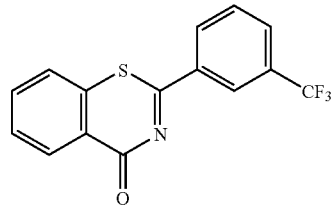

Thiosalicylic acid (2.91 g, 19 mmol) was suspended in isopropyl ether (40 ml). While stirring under ice cooling, pyridine (3.80 g, 48 mmol) and then 3-trifluorobenzoyl chloride (4.60 g, 22 mmol) were dropwise added to the suspension. After the reaction mixture was stirred for an hour at the same temperature, the mixture was diluted with water and 6N hydrochloric acid was added thereto to make its liquid property acidic. The mixture was extracted with ethyl acetate. The extract was washed with saturated brine and dried over anhydrous magnesium sulfate. The solvent was removed by distillation to give 2-[(3-trifluoromethylphenyl)carbonyl] thiobenzoic acid (7.30 g).

2-[(3-Trifluoromethylphenyl)carbonyl]thiobenzoic acid obtained above was suspended in acetone (40 ml). While stirring under ice cooling, triethylamine (1.60 g, 16 mmol) and then isobutyl chloroformate (2.58 g, 19 mmol) were dropwise added to the suspension. After stirring at the same temperature for 40 minutes, an aqueous solution (10 ml) of sodium azide (1.47 g, 22 mmol) was dropwise added to the reaction mixture, followed by further stirring for an hour. The reaction mixture was diluted with water and the dilution was extracted with toluene (30 ml×3). The extract was washed with saturated brine, dried over anhydrous magnesium sulfate and then filtered. The toluene solution was cooled to about −10° C. and a solution (6 ml) of tributylphosphine (6.07 g, 30 mmol) in toluene was dropwise added to the toluene solution. After completion of the dropwise addition, the reaction temperature was reverted to room temperature and the mixture was heated under reflux for 10 minutes. The reaction solution was applied to column chromatography using silica gel (150 g) to elute with hexane-ethyl acetate (2:1, v/v). The eluate was recrystallized from toluene-isopropyl ether to give the title compound (1.86 g, 32%).

Melting point: 114.6-114.7° C. Elemental analysis: as $C_{15}H_8NOSF_3$ Calcd.: C, 58.63; H, 2.62; N, 4.56 Found: C, 58.71; H, 2.73; N, 4.55

Example 21

Methyl 3-(4-oxo-4H-1,3-benzothiazin-2-yl)benzoate

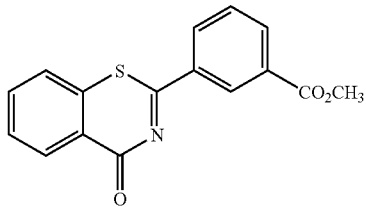

A mixture of methyl 3-cyanobenzoate (967 mg, 6.00 mmol), methyl thiosalicylate (1.51 g, 8.98 mmol), triethylamine (1.5 ml, 11 mmol) and xylene (6 mL) was stirred at 145° C. for 22 hours under a nitrogen flow. After the reaction mixture was allowed to cool, the crystals were taken by filtration and recrystallized from methanol to give the title compound (519 mg, 29%).

Melting point: 164.3-164.4° C. $^1$H-NMR (CDCl$_3$) δ: 3.98 (3H, s), 7.56-7.74 (4H, m), 8.30 (1H, dt, J 7.8, 1.4 Hz), 8.44 (1H, ddd, J=8.0, 2.0, 1.3 Hz), 8.53-8.58 (1H, m), 8.83 (1H, t, J=1.5 Hz). Elemental analysis: as $C_{16}H_{11}NO_3S$ Calcd.: C, 64.63; H, 3.73; N, 4.71 Found: C, 64.62; H, 3.64; N, 4.70

Example 22

Methyl 2-(benzoylamino)-3-[3-(4-oxo-4H-1,3-benzothiazin-2-yl)phenyl]propionate

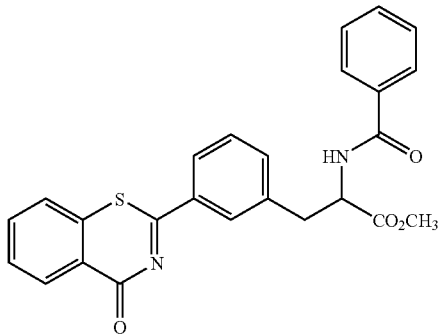

A mixture of methyl 2-(benzoylamino)-3-(3-cyanophenyl) propionate (201 mg, 0.652 mmol), methyl thiosalicylate (165 mg, 0.981 mmol), triethylamine (0.18 mL, 1.3 mmol) and xylene (0.65 ml) was stirred at 145° C. for 15 hours under a nitrogen flow. The reaction mixture was applied to silica gel column chromatography (gradient elution with hexane-ethyl acetate from 67:33 to 50:50). The eluate was crystallized from ethyl acetate-diisopropyl ether to give the title compound (49.7 mg, 17%).

Melting point: 130.9-131.0° C. $^1$H-NMR (CDCl$_3$) δ: 3.32 (1H, dd, J=13.9, 5.5 Hz), 3.44 (1H, dd, J=13.9, 5.5 Hz), 3.82 (3H, s), 5.15 (1H, dt, J=7.0, 5.5 Hz), 6.66 (1H, br d, J=7.0 Hz), 7.49-7.53 (6H, m), 7.59-7.71 (2H, m), 7.75-7.80 (2H, m), 8.02 (1H, t, J=1.5 Hz), 8.10 (1H, dt, J=7.3, 1.8 Hz), 8.51-8.56 (1H, m). Elemental analysis: as $C_{25}H_{20}N_2O_4S$ Calcd.: C, 67.55; H, 4.54; N, 6.30 Found: C, 67.53; H, 4.39; N, 6.00

REFERENCE EXAMPLE 14

2-(4-Chloro-2-methylphenyl)-4H-1,3-benzothiazin-4-one

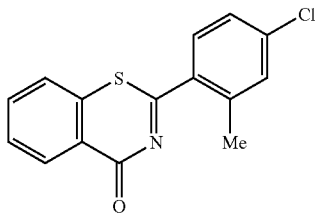

4-Chloro-2-methylbenzoic acid (5.00 g, 29 mmol) was dissolved in chloroform (30 ml) and thionyl chloride (10 ml) was added to the solution. The mixture was heated under reflux overnight. The reaction solution was concentrated under reduced pressure. While stirring under ice cooling, the concentrate was dropwise added to a mixture of thiosalicylic acid (4.00 g, 26 mmol), pyridine (5.13 g, 65 mmol) and tert-butylmethyl ether (50 ml). After the reaction mixture was stirred at the same temperature for 3 hours, the mixture was diluted with water and 6N hydrochloric acid was added thereto to make its liquid property acidic. The crystals precipitated were taken by filtration, washed with water and dried to give 2-[(4-chloro-2-methylphenyl)carbonyl]thiobenzoic acid (5.73 g, 72%).

2-[(4-Chloro-2-methylphenyl)carbonyl]thiobenzoic acid (5.50 g, 18 mmol) obtained above was suspended in acetone (80 ml). While stirring under ice cooling, triethylamine (1.81 g, 18 mmol) and then isobutyl chloroformate (2.73 g, 20 mmol) were dropwise added to the suspension. After stirring at the same temperature for an hour, an aqueous solution (10 ml) of sodium azide (1.30 g, 20 mmol) was dropwise added to the reaction mixture, followed by further stirring for an hour. The reaction mixture was diluted with water and the dilution was extracted with toluene (20 ml×3). The extract was washed with saturated brine, dried over anhydrous magnesium sulfate and then filtered. The toluene solution was cooled to about −10° C. and tributylphosphine (4.05 g, 20 mmol) was dropwise added to the solution. After completion of the dropwise addition, the reaction temperature was reverted to room temperature and the mixture was heated under reflux for 10 minutes. The reaction solution was concentrated under reduced pressure and recrystallized from ethyl acetate to give the title compound (0.75 g, 15%) as crystals.

Melting point: 134.1-134.2° C. $^1$H-NMR (CDCl$_3$) δ:2.55 (3H, s), 7.26-7.51 (2H, m), 7.51-7.71 (4H, m), 8.58 (1H, dd, J=1.5 Hz, 7.2 Hz). Elemental analysis: as $C_{15}H_{10}NOSCl$ Calcd.: C, 62.61; H, 3.50; N, 4.87 Found: C, 62.46; H, 3.37; N, 4.88

REFERENCE EXAMPLE 15

Methyl 2-(ethylamino)-4-(4-oxo-4H-1,3-benzothiazin-2-yl)benzoate

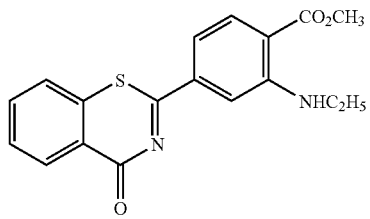

A mixture of methyl 4-cyano-2-(ethylamino)benzoate (1.23 g, 6.02 mmol), methyl thiosalicylate (1.52 g, 9.04 mmol), triethylamine (1.7 mL, 12 mmol) and xylene (6 mL) was stirred at 145° C. for 18 hours under a nitrogen flow. After the reaction mixture was allowed to cool, the crystals were taken by filtration and recrystallized from methanol to give the title compound (450 mg, 22%).

Melting point: 170.8-178.2° C. $^1$H-NMR (CDCl$_3$) δ: 1.37 (3H, t, J=7.2 Hz), 3.37 (2H, qd, J=7.2, 5.0 Hz), 3.90 (3H, s), 7.31 (1H, dd, J=8.6, 1.7 Hz), 7.48 (1H, d, J=1.7 Hz), 7.54-7.58 (1H, m), 7.61-7.80 (3H, m), 8.03 (1H, d, J=8.6 Hz), 8.54-8.58 (1H, m). Elemental analysis: as $C_{18}H_{16}N_2O_3S$ Calcd.: C, 63.51; H, 4.74; N, 8.23 Found: C, 63.65; H, 4.60; N, 8.03

Experimental Example 1

Cardiomyocyte Apoptosis Inhibitory Activity

Newborn rats (within 1 day after birth) were obtained from pregnant Wistar rats purchased from Charles River Japan, Inc., anesthetized under ether, and sterilized with 70% ethanol. Then the heart was excised with tweezers. The excised heart was washed with a phosphate buffered saline (T900; manufactured by Takara) and cut into pieces with surgical scissors. The tissue pieces were washed 4 to 5 times with a phosphate buffered saline to remove a majority of blood-derived non-myocardial cells. To the tissue pieces derived from 10 newborns, 5 ml of enzyme solution [solution prepared by dissolving trypsin (1.25 mg)(manufactured by Difco) and collagenase (0.25 mg)(manufactured by Sigma) in phosphate buffered saline (PBS)(1 ml)] was added and the mixture was stirred with a stirrer for 15 minutes while maintaining at 37° C. After 2.5 ml of the enzyme solution was added thereto, the mixture was stirred for further 15 minutes. This procedure was repeated twice. Subsequently, Medium 199 (manufactured by Gibson) containing 10% fetal calf serum (manufactured by Biowiker) was added in a half volume of the enzyme solution to terminate the enzyme reaction. The cells were filtered through a cell strainer (manufactured by Falcon) and then centrifuged at 400×g for 5 minutes to collect the cells.

The cells thus collected from the 10 newborns were suspended in 50 ml of Medium 199 containing 10% fetal calf serum. The suspension was plated onto 100 mm Petri dishes (manufactured by Iwaki) in a volume of 10 ml each/dish and cultured for 1 hour in a CO$_2$ incubator set at 5% CO$_2$ and 37° C. The cells were then recovered, filtered through a cell strainer and centrifuged at 400×g for 5 minutes to collect the primary cardiomyocytes derived from the newborn rats.

Then, the cardiomyocytes from the newborn rats (10) were suspended in 2 ml of hypotonic solution [prepared by dissolving NH$_4$Cl (8.29 g), KHCO$_3$ (1.0 g), 37 mg of EDTA/2Na (disodium ethylenediaminetetraacetate)(manufactured by Dojin Chemical Laboratory) in water (1 L)] and the suspension was allowed to stand for 3 minutes to disrupt erythrocytes. After 10 ml of Medium 199 containing 10% fetal calf serum was added thereto, the mixture was centrifuged at 400×g for 5 minutes to collect the primary cardiomyocytes from newborn rats. The cells were suspended in Medium 199 containing 10% fetal calf serum. The suspension was then filtered through a cell strainer. An aliquot of the resulting cardiomyocyte suspension was taken and 0.3% trypan blue was added thereto. The mixture was mildly mixed and the number of cardiomyocytes was counted with a hemocytometer.

The primary cardiomyocytes from the newborn rats were suspended at a density of 3×10$^6$ cells/ml in Medium 199 containing 10% fetal calf serum. The suspension was plated onto a 96-well plate in a volume of 0.1 ml/well, followed by incubation in a CO$_2$ incubator set at 5% CO$_2$ and 37° C. for a day. After the plate was stirred with a micromixer (manufactured by Taiyo Kagaku Kogyo), the medium was exchanged 3 times with serum-free Medium 199 and then test compounds were added thereto. The cells were cultured for further 4 days to induce apoptosis. Subsequently, fetal calf serum was added thereto at a concentration of 10%, and the cells were further cultured for about 17 hours in a CO$_2$ incubator set at 5% CO$_2$ and 37° C. The number of viable cells was determined with Cell Counting Kit (manufactured by Dojin Chemical Laboratory) using as a chromogen WST-8 [2-(2-methoxy-4-nitrophenyl)3-(4-nitrophenyl)-5-(2,4-disulfophenyl)-2H-tetrazolium, monosodium salt] to assess the cardiomyocyte apoptosis inhibitory activity.

The experiment described above was triplicated in an independent manner.

The mean minimum effective concentration (±SD) for each test compound is shown in TABLE 1. In the TABLE, the minimum effective concentration is defined as the concentration of the test compound required to increase the mean viable cell number by 50% as compared to that in the absence of any test compound.

TABLE 1

| Compound of EXAMPLE | Minimum Effective Concentration (μM) |
|---|---|
| 1 | 0.072 |
| 2 | 0.020 |
| 3 | 0.047 |
| 4 | 0.042 |
| 8 | 0.025 |
| 9 | 0.088 |
| 10 | 0.062 |
| 13 | 0.062 |
| 16 | 0.021 |
| 18 | 0.083 |

The results above reveal that the compounds of EXAMPLES have the cardiomyocyte apoptosis inhibitory activity.

Experimental Example 2

Antioxidant Response Element (ARE)-dependent Transcriptional Activation Activity (1) Construction of Luciferase Reporter Vector Bearing Antioxidant Response Element (ARE)

ARE-containing luciferase reporter vectors pGL3-ARE and pGL3-ARE 694G were constructed based on The Journal of Biological Chemistry, 266, 11632, 1991 and The Journal of Biological Chemistry, 275, 40134, 2000, by synthesizing ARE (SEQ ID NO: 1) for rat glutathione S-transferase Ya subunit gene and mutated ARE, i.e., mutant ARE (A694G) (SEQ ID NO: 2) oligonucleotide and then transfecting them to the NheI/BglII site of pGL3-Promoter Vector (manufactured by Promega Corp.), respectively.

(2) Assay for Antioxidant Response Element (ARE)-dependent Transcriptional Activation Activity Rat H9c2 cells were suspended in Dulbecco's modified Eagle's medium (10% FBS, D-MEM medium) containing 5% heat-inactivated fetal calf serum in $7 \times 10^4$ cells/ml. A 18 ml aliquot of the suspension was plated on a cell culture Petri dish, followed by incubation at 37° C. for about 16 hours under 5% $CO_2$. Using FuGENE6 Transfection reagent (manufactured by Roche), the cells were transfected with 36 l of luciferase reporter vector pGL3-ARE or pGL3-ARE 694G comprising ARE, and further incubated for about 7 hours. After completion of the incubation, the cells were recovered and suspended in 10% FBS-containing D-MEM in $1 \times 10^5$ cells/ml and 100 µl each of the suspension was plated in each well of a 96-well white opaque plate (manufactured by Falcon), followed by incubation at 37° C. for about 17 hours under 5% $CO_2$. Next, the cells were washed with D-MEM to remove serum, and D-MEM containing a test compound was added to the cells, followed by incubation at 37° C. for about 24 hours under 5% $CO_2$. After completion of the incubation, 80 µl of Steady-Glo Reagent (manufactured by Promega Corp.) was added to each well. After allowing to stand for 30 minutes, fluorescence levels by luciferase were determined using a WALLAC ARVO SX (manufactured by Perkin-Elmer). Taking the emitted luminescence of test compound-free group as 100%, the ARE-dependent transcriptional activation was shown in terms of the concentration of test compound, which caused to emit the luminescence of 200% ($EC_{200}$: µM). The results are shown in TABLE 2.

TABLE 2

| Compound of EXAMPLE | $EC_{200}$ (µM) |
|---|---|
| 20 | 1.5 |

The results reveal that the compound of the EXAMPLE exhibits the ARE-dependent transcriptional activation activity.

Preparation Example 1

| Capsules | |
|---|---|
| (1) Compound obtained in EXAMPLE 16 | 30 mg |
| (2) Lactose | 60 mg |
| (3) Crystalline cellulose | 9 mg |
| (4) Magnesium stearate | 1 mg |
| 1 Capsule | 100 mg |

After mixing (1), (2) and (3) and a half of (4), the mixture is granulated. The remaining (4) is added to the granules and the resulting mixture is sealed in gelatin capsules.

Preparation Example 2

| Tablets | |
|---|---|
| (1) Compound obtained in EXAMPLE 16 | 30 mg |
| (2) Lactose | 48 mg |
| (3) Corn starch | 18 mg |
| (4) Crystalline cellulose | 3.5 mg |
| (5) Magnesium stearate | 0.5 mg |
| 1 Tablet | 100 mg |

After mixing (1), (2), (3) and (4) and a half of (5), the mixture is granulated.

The remaining (4) and (5) are added to the granules and the resulting mixture is compressed under pressure to make tablets.

INDUSTRIAL APPLICABILITY

According to the present invention, there are provided novel 1,3-benzothiazinone derivatives, which have safe and excellent effects of cell death inhibition, MIF binding, etc. and are useful as prophylactic or therapeutic agents for cardiovascular diseases, bone or joint diseases, infectious diseases, inflammatory diseases, kidney diseases, etc.

The invention claimed is:

1. A compound represented by formula:

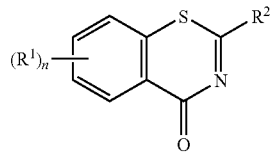

[wherein, $R^1$ represents (1) a halogen atom, (2) hydroxyl, (3) nitro, (4) an optionally halogenated $C_{1-6}$ alkyl, (5) a $C_{1-6}$ alkyl-carbonyl optionally having 1 to 5 substituents selected from (1') a halogen atom, (2') a $C_{1-3}$ alkylenedioxy (3') nitro, (4') cyano, (5') a $C_{1-6}$ alkyl which may be substituted with 1 to 5 halogen atoms, (6') a $C_{2-6}$ alkenyl which may be substituted with 1 to 5 halogen atoms, (7') a carboxy-$C_{2-6}$ alkenyl, (8') a $C_{2-6}$ alkynyl which may be substituted with 1 to 5 halogen atoms, (9') a $C_{3-8}$ cycloalkyl which may be substituted with 1 to 5 halogen atoms, (10') a $C_{6-14}$ aryl, (11') a $C_{1-6}$ alkoxy which may be substituted with 1 to 5 halogen atoms, (12') a $C_{1-6}$ alkoxy-carbonyl-$C_{1-6}$ alkoxy, (13') hydroxyl, (14') a $C_{6-14}$ aryloxy, (15') a $C_{7-16}$ aralkyloxy, (16') mercapto, (17') a $C_{1-6}$ alkylthio which may be substituted with 1 to 5 halogen atoms, (18') a $C_{6-14}$ arylthio, (19') a $C_{7-16}$ aralkylthio, (20') amino, (21') a mono-$C_{1-6}$ alkylamino, (22') a mono-$C_{6-14}$ arylamino, (23') a di-$C_{1-6}$ alkylamino, (24') a di-$C_{6-14}$ arylamino, (25') formyl, (26') carboxy, (27') a $C_{1-6}$ alkyl-carbonyl, (28') a $C_{3-8}$ cycloalkyl-carbonyl, (29') a $C_{1-6}$ alkoxy-carbonyl, (30') a $C_{6-14}$ aryl-carbonyl, (31') a $C_{7-16}$ aralkyl-carbonyl, (32') a $C_{6-14}$ aryloxy-carbonyl, (33') a $C_{7-16}$ aralkyloxy-carbonyl, (34') a 5- or 6-membered heterocyclic carbonyl, (35') carbamoyl, (36') a mono-$C_{1-6}$ alkyl-carbamoyl, (37') a di-$C_{1-6}$ alkyl-carbamoyl, (38') a mono-$C_{6-14}$ aryl-carbamoyl, (39') a 5- or 6-membered heterocyclic carbamoyl, (40') a $C_{1-6}$ alkylsulfonyl, (41') a $C_{6-14}$ arylsulfonyl, (42') formylamino, (43') a $C_{1-6}$ alkyl-carbonylamino, (44') a $C_{6-14}$ aryl-carbonylamino, (45') a $C_{1-6}$ alkoxy-carbonylamino, (46') a $C_{1-6}$ alkylsulfonylamino, (47') a $C_{6-14}$ arylsulfonylamino, (48') a $C_{1-6}$ alkyl-carbonyloxy, (49') a $C_{6-14}$ aryl-carbonyloxy, (50') a $C_{1-6}$ alkoxy-carbonyloxy, (51') a mono-$C_{1-6}$alkyl-carbamoyloxy, (52') a di-$C_{1-6}$alkyl-carbamoyloxy, (53') a mono-$C_{6-14}$ aryl-carbamoyloxy, (54') nicotinoyloxy, (55') a 5- to 7-membered saturated cyclic amino, (56') a 5- to 10-membered aromatic heterocyclic group and (57') sulfo (hereinafter simply referred to as Substituent group A);

(6) a $C_{2-6}$ alkenyl-carbonyl optionally having 1 to 5 substituents selected from the Substituent group A;

(7) a $C_{2-6}$ alkynyl-carbonyl optionally having 1 to 5 substituents selected from the Substituent group A;

(8) a $C_{3-8}$ cycloalkyl-carbonyl optionally having 1 to 5 substituents selected from the Substituent group A;

(9) a $C_{6-14}$ aryl-carbonyl optionally having 1 to 5 substituents selected from the Substituent group A;

(10) a $C_{7-16}$ aralkyl-carbonyl optionally having 1 to 5 substituents selected from the Substituent group A;

(11) a 5- to 14-membered heterocyclic carbonyl containing 1 to 4 hetero atoms, which are 1 or 2 different atoms selected from nitrogen, sulfur and oxygen atoms, in addition to carbon atoms (this heterocyclic carbonyl may have 1 to 5 substituents selected from the Substituent group A);

(12) an amino optionally having 1 or 2 substituents selected from (1') a $C_{1-6}$ alkyl optionally having 1 to 5 substituents selected from the Substituent group A, (2') a $C_{2-6}$ alkenyl optionally having 1 to 5 substituents selected from the Substituent group A, (3') a $C_{2-6}$ alkynyl optionally having 1 to 5 substituents selected from the Substituent group A, (4') a $C_{3-8}$ cycloalkyl optionally having 1 to 5 substituents selected from the Substituent group A, (5') a $C_{6-14}$ aryl optionally having 1 to 5 substituents selected from the Substituent group A, (6') a $C_{7-16}$ aralkyl optionally having 1 to 5 substituents selected from the Substituent group A, (7') a 5- to 14-membered heterocyclic group containing 1 to 4 hetero atoms, which are 1 or 2 different atoms selected from nitrogen, sulfur and oxygen atoms, in addition to carbon atoms, (8') a $C_{1-6}$ alkyl-carbonyl optionally having 1 to 5 substituents selected from the Substituent group A, (9') a $C_{2-6}$ alkenyl-carbonyl optionally having 1 to 5 substituents selected from the Substituent group A, (10') a $C_{2-6}$ alkynyl-carbonyl optionally having 1 to 5 substituents selected from the Substituent group A, (11') a $C_{3-8}$ cycloalkyl-carbonyl optionally having 1 to 5 substituents selected from the Substituent group A, (12') a $C_{6-14}$ aryl-carbonyl optionally having 1 to 5 substituents selected from the Substituent group A, (13') a $C_{7-16}$ aralkyl-carbonyl optionally having 1 to 5 substituents selected from the Substituent group A and (14') a 5- to 14-membered heterocyclic carbonyl containing 1 to 4 hetero atoms, which are 1 or 2 different atoms selected from nitrogen, sulfur and oxygen atoms, in addition to carbon atoms;

$R^2$ is a group represented by formula:

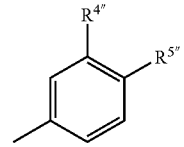

(wherein $R^{4\prime\prime\prime}$ represents hydrogen atom or cyano, and $R^{5\prime\prime\prime}$ represents hydrogen atom, a $C_{1-6}$ alkyl-carbonyl or a $C_{1-6}$ alkyl-carbonylamino: provided that $R^{4\prime\prime\prime}$ and $R^{5\prime\prime\prime}$ cannot both be hydrogen atoms at the same time); and, n is an integer of 0 to 4], or a salt thereof.

2. A 1,3-benzothiazinone derivative, which is
2-(3-cyanophenyl)-4H-1,3-benzothiazin-4-one,
2-(4-acetylphenyl)-4H-1,3-benzothiazin-4-one,
2-(4-methylsulfonylphenyl)-4H-1,3-benzothiazin-4-one,
2-(4-acetylaminophenyl)-4H-1,3-benzothiazin-4-one, or
2-(3-trifluoromethylphenyl)-4H-1,3-benzothiazin-4-one.

3. A pharmaceutical composition comprising the compound according to claim 1 and a pharmaceutically acceptable carrier.

4. A compound represented by formula:

wherein, $R^2$ represents a group represented by formula:

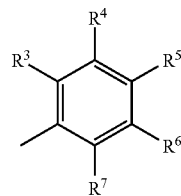

wherein, one of $R^3$ and $R^7$ represents hydrogen atom, and the other is a $C_{1-6}$ alkyl optionally having 1 to 5 substituents selected from the Substituent group A or a $C_{1-6}$ alkoxy optionally selected from the Substituent group A; and $R^4$, $R^5$ and $R^6$ each represents hydrogen atom; one of $R^4$ and $R^6$ represents hydrogen atom, and the other is a bromine atom, cyano, an alkyl having a substituent selected from carboxy, a halogen atom, an alkoxycarbonyl and an arylcarbonylamino, a $C_{1-6}$ alkoxy optionally having 1 to 5 substituents selected from the Substituent group A, an optionally substituted amino or alkoxycarbonyl and $R^3$, $R^7$ and $R^5$ each represents hydrogen atom; and $R^5$ represents hydroxy, cyano, an alkyl substituted with a halogen atom, aryl, an acyl, a carbamoyl optionally having 1 or 2 substituents selected from (1') a $C_{1-6}$ alkyl optionally having 1 to 5 substituents selected from the Substituent group A, (2') a $C_{2-6}$ alkenyl optionally having 1 to 5 substituents selected from the Substituent group A, (3') a $C_{2-6}$ alkynyl optionally having 1 to 5 substituents selected from the Substituent group A, (4') a $C_{3-8}$ cycloalkyl optionally having 1 to 5 substituents selected from the Substituent group A, (5') a $C_{6-14}$ aryl optionally having 1 to 5 substituents selected from the Substituent group A, (6') a $C_{7-16}$ aralkyl optionally having 1 to 5 substituents selected from the Substituent group A, (7') a 5- to 14-membered heterocyclic carbonyl containing 1 to 4 hetero atoms, which are 1 or 2 different atoms selected from nitrogen, sulfur and oxygen atoms, in addition to carbon atoms, (8') a $C_{1-6}$ alkyl-carbonyl optionally having 1 to 5 substituents selected from the Substituent group A, (9') a $C_{2-6}$ alkenyl-carbonyl optionally having 1 to 5 substituents selected from the Substituent group A, (10') a $C_{2-6}$ alkynyl-carbonyl optionally having 1 to 5 substituents selected from the Substituent group A, (11') a $C_{3-8}$ cycloalkyl-carbonyl optionally having 1 to 5 substituents selected from the Substituent group A, (12') a $C_{6-14}$ aryl-carbonyl optionally having 1 to 5 substituents selected from the Substituent group A, (13') a $C_{7-16}$ aralkyl-carbonyl optionally having 1 to 5 substituents selected from the Substituent group A and (14') a 5- to 14-membered heterocyclic carbonyl containing 1 to 4 hetero atoms, which are 1 or 2 different atoms selected from nitrogen, sulfur and oxygen atoms, in addition to carbon atoms, or an amino optionally having 1 or 2 substituents selected from (1') a $C_{1-6}$ alkyl optionally having 1 to 5 substituents selected from the Substituent group A, (2') a $C_{2-6}$ alkenyl optionally having 1 to 5 substituents selected from the Substituent group A and $R^3$, $R^4$, $R^6$ and $R^7$ each represents hydrogen atom, or a salt thereof;

wherein Substituent group A is (1') a halogen atom, (2') a $C_{1-3}$ alkylenedioxy (3') nitro, (4') cyano, (5') a $C_{1-6}$ alkyl which may be substituted with 1 to 5 halogen atoms, (6') a $C_{2-6}$ alkenyl which may be substituted with 1 to 5 halogen atoms, (7') a carboxy-$C_{2-6}$ alkenyl, (8') a $C_{2-6}$ alkynyl which may be substituted with 1 to 5 halogen atoms, (9') a $C_{3-8}$ cycloalkyl which may be substituted with 1 to 5 halogen atoms, (10') a $C_{6-14}$ aryl, (11') a $C_{1-6}$ alkoxy which may be substituted with 1 to 5 halogen atoms, (12') a $C_{1-6}$ alkoxy-carbonyl-$C_{1-6}$ alkoxy, (13') hydroxyl, (14') a $C_{6-14}$ aryloxy, (15') a $C_{7-16}$ aralkyloxy, (16') mercapto, (17') a $C_{1-6}$ alkylthio which may be substituted with 1 to 5 halogen atoms, (18') a $C_{6-14}$ arylthio, (19') a $C_{7-16}$ aralkylthio, (20') amino, (21') a mono-$C_{1-6}$ alkylamino, (22') a mono-$C_{6-14}$ arylamino, (23') a di-$C_{1-6}$ alkylamino, (24') a di-$C_{6-14}$ arylamino, (25') formyl, (26') carboxy, (27') a $C_{1-6}$ alkyl-carbonyl, (28') a $C_{3-8}$ cycloalkyl-carbonyl, (29') a $C_{1-6}$ alkoxy-carbonyl, (30') a $C_{6-14}$ aryl-carbonyl, (31') a $C_{7-16}$ aralkyl-carbonyl, (32') a $C_{6-14}$ aryloxy-carbonyl, (33') a $C_{7-16}$ aralkyloxy-carbonyl, (34') a 5- or 6-membered heterocyclic carbonyl, (35') carbamoyl, (36') a mono-$C_{1-6}$ alkyl-carbamoyl, (37') a di-$C_{1-6}$ alkyl-carbamoyl, (38') a mono-$C_{6-14}$ aryl-carbamoyl, (39') a 5- or 6-membered heterocyclic carbamoyl, (40') a $C_{1-6}$ alkylsulfonyl, (41') a $C_{6-14}$ arylsulfonyl, (42') formylamino, (43') a $C_{1-6}$ alkyl-carbonylamino, (44') a $C_{6-14}$ aryl-carbonylamino, (45') a $C_{1-6}$ alkoxy-carbonylamino, (46') a $C_{1-6}$ alkylsulfonylamino, (47') a $C_{6-14}$ arylsulfonylamino, (48') a $C_{1-6}$ alkyl-carbonyloxy, (49') a $C_{6-14}$ aryl-carbonyloxy, (50') a $C_{1-6}$ alkoxy-carbonyloxy, (51') a mono-$C_{1-6}$alkyl-carbamoyloxy, (52') a di-$C_{1-6}$alkyl-carbamoyloxy, (53') a mono-$C_{6-14}$ aryl-carbamoyloxy, (54') nicotinoyloxy, (55') a 5- to 7-membered saturated cyclic amino, (56') a 5- to 10-membered aromatic heterocyclic group and (57') sulfo.

5. The compound according to claim 4, wherein one of $R^4$ and $R^6$ represents hydrogen atom, and the other is bromine atom, (iv) hydroxyl, (v) cyano, (vi) a carboxy-substituted alkyl, (vii) a $C_{1-6}$ alkoxy optionally having 1 to 5 substituents selected from the Substituent group A, or an amino optionally having 1 or 2 substituents selected from (1') a $C_{1-6}$ alkyl optionally having 1 to 5 substituents selected from the Substituent group A, (2') a $C_{2-6}$ alkenyl optionally having 1 to 5 substituents selected from the Substituent group A and $R^3$, $R^7$ and $R^5$ each represents hydrogen atom.

6. The compound according to claim 4, wherein, $R^2$ represents: a group represented by formula:

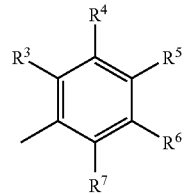

wherein: (I) one of $R^3$ and $R^7$ represents: hydrogen atom, and the other is a $C_{1-6}$ alkyl optionally having 1 to 5 substituents selected from the Substituent group A, wherein Substituent group A consists of a $C_{1-6}$ alkyl-carbonyl optionally having 1 to 5 1'substituents selected from (1') a halogen atom, (2') a $C_{1-3}$ alkylenedioxy, (3') nitro, (4') cyano, (5') a $C_{1-6}$ alkyl which may be substituted with 1 to 5 halogen atoms, (6') a $C_{2-6}$ alkenyl which may be substituted with 1 to 5 halogen atoms, (7') a carboxy-$C_{2-6}$ alkenyl, (8') a $C_{2-6}$ alkynyl which may be substituted with 1 to 5 halogen atoms, (9') a $C_{3-8}$ cycloalkyl which may be substituted with 1 to 5 halogen atoms, (10') a $C_{6-14}$ aryl, (11') a $C_{1-6}$ alkoxy which may be substituted with 1 to 5 halogen atoms, (12') a $C_{1-6}$ alkoxy-carbonyl-$C_{1-6}$ alkoxy, (13') hydroxyl, (14') a $C_{6-14}$ aryloxy, (15') a $C_{7-16}$ aralkyloxy, (16') mercapto, (17') a $C_{1-6}$ alkylthio which may be substituted with 1 to 5 halogen atoms, (18') a $C_{6-14}$ arylthio, (19') a $C_{7-16}$ aralkylthio, (20') amino, (21') a mono-$C_{1-6}$ alkylamino, (22') a mono-$C_{6-14}$ arylamino, (23') a di-$C_{1-6}$ alkylamino, (24') a di-$C_{6-14}$ arylamino, (25') formyl, (26') carboxy, (27') a $C_{1-6}$ alkyl-carbonyl, (28') a $C_{3-8}$ cycloalkyl-carbonyl, (29') a $C_{1-6}$ alkoxy-carbonyl, (30') a $C_{6-14}$ aryl-carbonyl, (31') a $C_{7-16}$ aralkyl-carbonyl, (32') a $C_{6-14}$ aryloxy-carbonyl, (33') a $C_{7-16}$ aralkyloxy-carbonyl, (34') a 5-or 6-membered heterocyclic carbonyl, (35') carbamoyl, (36') a mono-$C_{1-6}$ alkyl-carbamoyl, (37') a di-C1-6alkyl-carbamoyl, (38') a mono-$C_{6-14}$ aryl-carbamoyl, (39') a 5- or 6-membered heterocyclic carbamoyl, (40') a $C_{1-6}$ alkylsulfonyl, (41') a $C_{6-14}$ arylsulfonyl, (42') formylamino, (43') a $C_{1-6}$ alkyl-carbonylamino, (44') a $C_{6-14}$ aryl-carbonylamino, (45') a $C_{1-6}$ alkoxy-carbonylamino, (46') a $C_{1-6}$ alkylsulfonylamino, (47') a $C_{6-14}$ arylsulfonylamino, (48') a $C_{1-6}$ alkyl-carbonyloxy, (49') a $C_{6-14}$ aryl-carbonyloxy, (50') a $C_{1-6}$ alkoxy-carbonyloxy, (51') a mono-$C_{1-6}$ alkyl-carbamoyloxy, (52') a di-$C_{1-6}$ alkyl-carbamoyloxy, (53') a mono-$C_{6-14}$ aryl-carbamoyloxy, (54') nicotinoyloxy, (55') a 5- to 7-membered saturated cyclic amino, (56') a 5- to 10-membered aromatic heterocyclic group and (57') sulfo; a $C_{1-6}$ alkoxy optionally having 1 to 5 substituents selected from Substituent group A;

and $R^4$, $R^5$ and R6 each represents hydrogen atom; or (II) one of $R^4$ and $R^6$ each independently represents: hydrogen atom; and the other is bromine atom; cyano; a $C_{1-6}$ alkyl having 1 to 3 substituents selected from carboxy, a halogen atom, a $C_{1-6}$ alkoxy-carbonyl and a $C_{6-14}$ aryl-carbonylamino; a $C_{1-6}$ alkoxy optionally having 1 to 5 substituents selected from the Substituent group A, an amino having a $C_{1-6}$ alkyl-carbonyl, a $C_{1-6}$ alkoxy-carbonyl or (III) $R^5$ represents: hydroxy; cyano; a $C_{1-6}$ alkyl substituted with 1 to 5 halogen atoms; a $C_{6-14}$ aryl; a $C_{1-6}$ alkyl-carbonyl; a carbamoyl having 2 $C_{1-6}$ alkyl groups or an amino having a $C_{1-6}$ alkyl-carbonyl group.

7. The compound according to claim 4, wherein $R^2$ is a group represented by formula:

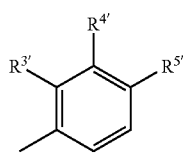

(wherein (1) $R^{3'}$ represents a $C_{1-6}$ alkoxy or a $C_{1-6}$ alkyl substituted with 1 to 5 halogen atoms, and $R^{4'}$ and $R^{5'}$ each represents hydrogen atom; (2) $R^{4'}$ represents bromine atom, cyano, a $C_{1-6}$ alkyl having 1 to 3 substituents selected from carboxy, a halogen atom, a $C_{1-6}$ alkoxy-carbonyl and a $C_{6-14}$ aryl-carbonylamino, a $C_{1-6}$ alkoxy substituted with a $C_{1-6}$ alkoxy-carbonyl or a $C_{1-6}$ alkyl-carbonylamino, and $R^{3'}$ and $R^{5'}$ each represents hydrogen atom; or (3) $R^{5'}$ represents hydroxy, cyano, a $C_{1-6}$ alkyl substituted with 1 to 5 halogen atoms, a $C_{6-14}$ aryl, a $C_{1-6}$ alkyl-carbonyl, a di-$C_{1-6}$ alkylcarbamoyl or a $C_{1-6}$ alkyl-carbonylamino, and $R^{3'}$ and $R^{4'}$ each represents hydrogen atom).

8. The compound according to claim 7, wherein $R^2$ is a group represented by formula:

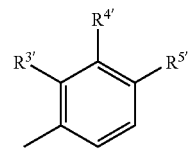

(wherein (1) $R^{3'}$ represents a $C_{1-6}$ alkoxy or a $C_{1-6}$ alkyl substituted with 1 to 5 halogen atoms, and $R^{4'}$ and $R^{5'}$ each represents hydrogen atom; (2) $R^{4'}$ represents bromine atom, cyano, a $C_{1-6}$ alkyl having 1 to 3 substituents selected from carboxy, a halogen atom, a $C_{1-6}$ alkoxy-carbonyl and a $C_{6-14}$ alyl-carbonylamino, a $C_{1-6}$ alkoxy substituted with a $C_{1-6}$ alkoxy-carbonyl or a $C_{1-6}$ alkyl-carbonylamino, and $R^{3'}$ and $R^{5'}$ each represents hydrogen atom; or (3) $R^{5'}$ represents hydroxy, cyano, a $C_{1-6}$ alkyl substituted with 1 to 5 halogen atoms, a $C_{6-14}$ aryl, a $C_{1-6}$ alkyl-carbonyl, a di-$C_{1-6}$ alkylcarbamoyl or a $C_{1-6}$ alkyl-carbonylamino, and $R^{3'}$ and $R^{4'}$ each represents hydrogen atom.

9. The compound according to claim 7, wherein $R^2$ is a group represented by formula:

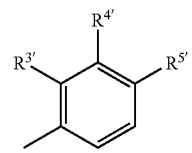

(wherein (1) $R^{3'}$ represents a $C_{1-6}$ alkyl substituted with 1 to 5 halogen atoms, and $R^{4'}$ and $R^{5'}$ each represents hydrogen atom; (2) $R^{4'}$ represents cyano, a $C_{1-6}$ alkyl having 1 to 3 substituents selected from carboxy, a halogen atom, a $C_{1-6}$ alkoxy-carbonyl and a $C_{6-14}$ aryl-carbonylamino, a $C_{1-6}$ alkoxy substituted with a $C_{1-6}$ alkoxy-carbonyl or a $C_{1-6}$ alkyl-carbonylamino, and $R^{3'}$ and $R^{5'}$ each represents hydrogen atom; or (3) $R^{5'}$ represents cyano, a $C_{1-6}$ alkyl substituted with 1 to 5 halogen atoms, a $C_{6-14}$ alyl or a $C_{1-6}$ alkyl-carbonylamino, and $R^{3'}$ and $R^{4'}$ represents hydrogen atom.

10. The compound according to claim 4, wherein $R^2$ is a group represented by formula:

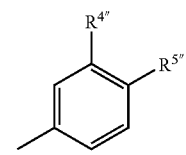

(wherein (1) $R^{4''}$ represents cyano and $R^{5''}$ represents hydrogen atom, or (2) $R^{4''}$ represents hydrogen atom and $R^{5''}$ represents a $C_{1-6}$ alkyl-carbonyl or a $C_{1-6}$ alkyl-1 carbonylamino).

11. A pharmaceutical composition comprising the compound according to claim 4 and a pharmaceutically acceptable carrier.

* * * * *